(12) United States Patent
Shenoy et al.

(10) Patent No.: US 9,468,466 B1
(45) Date of Patent: Oct. 18, 2016

(54) METHOD AND APPARATUS FOR ALTERING BIOMECHANICS OF THE SPINE

(71) Applicant: Cotera, inc., Menlo Park, CA (US)

(72) Inventors: Vivek Shenoy, Redwood City, CA (US); Hanson S. Gifford, III, Woodside, CA (US); Mark Deem, Mountain View, CA (US)

(73) Assignee: Cotera, Inc., Menlo Park, CA (US)

( * ) Notice: Subject to any disclaimer, the term of this patent is extended or adjusted under 35 U.S.C. 154(b) by 261 days.

(21) Appl. No.: 13/974,930

(22) Filed: Aug. 23, 2013

Related U.S. Application Data

(60) Provisional application No. 61/693,140, filed on Aug. 24, 2012, provisional application No. 61/792,720, filed on Mar. 15, 2013.

(51) Int. Cl.
*A61F 2/44* (2006.01)
*A61B 17/70* (2006.01)
*A61B 17/88* (2006.01)

(52) U.S. Cl.
CPC ............... *A61B 17/70* (2013.01); *A61B 17/88* (2013.01)

(58) Field of Classification Search
CPC ............. A61B 17/70; A61B 17/7055; A61B 17/8685; A61B 17/1671; A61B 17/1757
USPC .............. 606/246–249, 90; 623/17.11–17.16
See application file for complete search history.

(56) References Cited

U.S. PATENT DOCUMENTS

| | | |
|---|---|---|
| 2,632,440 A | 3/1953 | Hauser |
| 2,877,033 A | 3/1959 | Koetke |
| 3,242,922 A | 3/1966 | Thomas |
| 3,648,294 A | 3/1972 | Shahrestani |
| 3,681,786 A | 8/1972 | Lynch |
| 3,779,654 A | 12/1973 | Horne |
| 3,872,519 A | 3/1975 | Giannestras et al. |
| 3,875,594 A | 4/1975 | Swanson |
| 3,879,767 A | 4/1975 | Stubstad |
| 3,886,599 A | 6/1975 | Schlein |
| 3,889,300 A | 6/1975 | Smith |
| 3,902,482 A | 9/1975 | Taylor |
| 3,964,106 A | 6/1976 | Hutter, Jr. et al. |
| 3,988,783 A | 11/1976 | Treace |
| 4,007,495 A | 2/1977 | Frazier |
| 4,041,550 A | 8/1977 | Frazier |

(Continued)

FOREIGN PATENT DOCUMENTS

| | | |
|---|---|---|
| CA | 1205602 | 6/1986 |
| CN | 2788765 | 6/2006 |

(Continued)

OTHER PUBLICATIONS

Office Action dated Dec. 19, 2014, in connection with related U.S. Appl. No. 13/843,128, filed Mar. 15, 2013, Shenoy.

(Continued)

*Primary Examiner* — Mary Hoffman
*Assistant Examiner* — Tara R Carter
(74) *Attorney, Agent, or Firm* — Downs Rachlin Martin PLLC

(57) ABSTRACT

Pathology of the human spine can arise from excessive and/or uneven loading of regions within the spinal vertebrae and the intervertebral disc. Methods and apparatus are disclosed that enable displacement of soft tissue around the spine in a less invasive manner, thereby altering the mechanical load distribution within the spine to achieve a therapeutic effect.

5 Claims, 19 Drawing Sheets

(56) References Cited

U.S. PATENT DOCUMENTS

| | | |
|---|---|---|
| 4,052,753 A | 10/1977 | Dedo |
| 4,054,955 A | 10/1977 | Seppo |
| 4,069,518 A | 1/1978 | Groth, Jr. et al. |
| 4,156,944 A | 6/1979 | Schreiber et al. |
| 4,158,894 A | 6/1979 | Worrell |
| 4,164,793 A | 8/1979 | Swanson |
| 4,187,841 A | 2/1980 | Knutson |
| 4,246,660 A | 1/1981 | Wevers |
| 4,285,070 A | 8/1981 | Averill |
| 4,308,863 A | 1/1982 | Fischer |
| 4,353,361 A | 10/1982 | Foster |
| 4,367,562 A | 1/1983 | Gauthier |
| 4,470,158 A | 9/1984 | Pappas et al. |
| 4,501,266 A | 2/1985 | McDaniel |
| 4,570,625 A | 2/1986 | Harris |
| 4,576,158 A | 3/1986 | Boland |
| 4,621,627 A | 11/1986 | DeBastiani et al. |
| 4,637,382 A | 1/1987 | Walker |
| 4,642,122 A | 2/1987 | Steffee |
| 4,696,293 A | 9/1987 | Ciullo |
| 4,759,765 A | 7/1988 | Van Kampen |
| 4,759,766 A | 7/1988 | Buettner-Janz et al. |
| 4,776,851 A | 10/1988 | Bruchman et al. |
| 4,846,842 A | 7/1989 | Connolly et al. |
| 4,863,471 A | 9/1989 | Mansat |
| 4,871,367 A | 10/1989 | Christensen et al. |
| 4,873,967 A | 10/1989 | Sutherland |
| 4,883,486 A | 11/1989 | Kapadia et al. |
| 4,904,261 A | 2/1990 | Dove et al. |
| 4,919,672 A | 4/1990 | Millar et al. |
| 4,923,471 A | 5/1990 | Morgan |
| 4,942,875 A | 7/1990 | Hlavacek et al. |
| 4,955,915 A | 9/1990 | Swanson |
| 4,959,065 A | 9/1990 | Arnett et al. |
| 4,988,349 A | 1/1991 | Pennig |
| 4,988,350 A | 1/1991 | Herzberg |
| 5,002,574 A | 3/1991 | May et al. |
| 5,011,497 A | 4/1991 | Persson et al. |
| 5,019,077 A | 5/1991 | DeBastiani et al. |
| 5,019,104 A | 5/1991 | Whiteside et al. |
| 5,026,372 A | 6/1991 | Sturtzkopf et al. |
| 5,035,700 A | 7/1991 | Kenna |
| 5,041,112 A | 8/1991 | Mingozzi et al. |
| 5,100,403 A | 3/1992 | Hotchkiss et al. |
| 5,103,811 A | 4/1992 | Crupi |
| 5,121,742 A | 6/1992 | Engen |
| 5,152,280 A | 10/1992 | Danieli |
| 5,152,790 A | 10/1992 | Rosenberg et al. |
| 5,197,966 A | 3/1993 | Sommerkamp |
| 5,197,986 A | 3/1993 | Mikhail |
| 5,231,977 A | 8/1993 | Graston |
| 5,258,032 A | 11/1993 | Bertin |
| 5,304,180 A | 4/1994 | Slocum |
| 5,314,481 A | 5/1994 | Bianco |
| 5,318,567 A | 6/1994 | Vichard |
| 5,326,364 A | 7/1994 | Clift, Jr. et al. |
| 5,352,190 A | 10/1994 | Fischer |
| 5,375,823 A | 12/1994 | Navas |
| 5,383,937 A | 1/1995 | Mikhail |
| 5,405,347 A | 4/1995 | Lee et al. |
| 5,415,661 A | 5/1995 | Holmes |
| 5,425,775 A | 6/1995 | Kovacevic et al. |
| 5,456,722 A | 10/1995 | McLeod et al. |
| 5,480,443 A | 1/1996 | Elias |
| 5,540,688 A | 7/1996 | Navas |
| 5,545,229 A | 8/1996 | Parsons et al. |
| 5,571,198 A | 11/1996 | Drucker et al. |
| 5,575,819 A | 11/1996 | Amis |
| 5,578,038 A | 11/1996 | Slocum |
| 5,580,353 A | 12/1996 | Mendes et al. |
| 5,601,553 A | 2/1997 | Trebing et al. |
| 5,624,440 A | 4/1997 | Huebner |
| 5,662,648 A | 9/1997 | Faccioli et al. |
| 5,662,650 A | 9/1997 | Bailey et al. |
| 5,676,667 A | 10/1997 | Hausman |
| 5,681,313 A | 10/1997 | Diez |
| 5,695,496 A | 12/1997 | Orsak et al. |
| 5,702,460 A | 12/1997 | Carls et al. |
| 5,702,465 A | 12/1997 | Burkinshaw |
| 5,702,467 A | 12/1997 | Gabriel et al. |
| 5,716,357 A | 2/1998 | Rogozinski |
| 5,733,287 A | 3/1998 | Tepic et al. |
| 5,749,872 A | 5/1998 | Kyle et al. |
| 5,766,251 A | 6/1998 | Koshino |
| 5,803,924 A | 9/1998 | Oni et al. |
| 5,824,106 A | 10/1998 | Fournol |
| 5,871,540 A | 2/1999 | Weissman et al. |
| 5,873,843 A | 2/1999 | Draper |
| 5,879,386 A | 3/1999 | Jore |
| 5,888,203 A | 3/1999 | Goldberg |
| 5,928,234 A | 7/1999 | Manspeizer |
| 5,976,125 A | 11/1999 | Graham |
| 5,976,136 A | 11/1999 | Bailey et al. |
| 6,036,691 A | 3/2000 | Richardson |
| 6,096,040 A | 8/2000 | Esser |
| 6,113,637 A | 9/2000 | Gill et al. |
| 6,132,468 A | 10/2000 | Mansmann |
| 6,139,550 A | 10/2000 | Michelson |
| 6,143,032 A | 11/2000 | Schafer et al. |
| 6,146,423 A | 11/2000 | Cohen et al. |
| 6,161,080 A | 12/2000 | Aouni-Ateshian et al. |
| 6,162,223 A | 12/2000 | Orsak et al. |
| 6,176,860 B1 | 1/2001 | Howard |
| 6,193,225 B1 | 2/2001 | Watanabe |
| 6,200,347 B1 | 3/2001 | Anderson et al. |
| D443,060 S | 5/2001 | Benirschke et al. |
| 6,245,110 B1 | 6/2001 | Grundei et al. |
| 6,264,696 B1 | 7/2001 | Reigner et al. |
| 6,277,124 B1 | 8/2001 | Haag |
| 6,280,474 B1 | 8/2001 | Cassidy et al. |
| 6,302,915 B1 | 10/2001 | Cooney, III et al. |
| 6,315,798 B1 | 11/2001 | Ashby et al. |
| 6,315,852 B1 | 11/2001 | Magrini et al. |
| 6,355,037 B1 | 3/2002 | Crosslin et al. |
| 6,364,881 B1 | 4/2002 | Apgar et al. |
| 6,368,326 B1 | 4/2002 | Dakin et al. |
| 6,371,985 B1 | 4/2002 | Goldberg |
| 6,409,729 B1 | 6/2002 | Martinelli et al. |
| 6,409,767 B1 | 6/2002 | Perice et al. |
| 6,468,314 B2 | 10/2002 | Schwartz et al. |
| 6,482,232 B1 | 11/2002 | Boucher et al. |
| 6,485,503 B2 | 11/2002 | Jacobs et al. |
| 6,494,914 B2 | 12/2002 | Brown et al. |
| 6,520,964 B2 | 2/2003 | Tallarida et al. |
| 6,527,733 B1 | 3/2003 | Ceriani et al. |
| 6,540,708 B1 | 4/2003 | Manspeizer |
| 6,572,653 B1 | 6/2003 | Simonson |
| 6,579,318 B2 | 6/2003 | Varga et al. |
| 6,589,248 B1 | 7/2003 | Hughes |
| 6,592,622 B1 | 7/2003 | Ferguson |
| 6,599,321 B2 | 7/2003 | Hyde, Jr. |
| 6,599,322 B1 | 7/2003 | Amrich et al. |
| 6,616,696 B1 | 9/2003 | Merchant |
| 6,620,332 B2 | 9/2003 | Amrich |
| 6,623,486 B1 | 9/2003 | Weaver et al. |
| 6,626,945 B2 | 9/2003 | Simon et al. |
| 6,632,247 B2 | 10/2003 | Boyer, II et al. |
| 6,652,529 B2 | 11/2003 | Swanson |
| 6,663,631 B2 | 12/2003 | Kuntz |
| 6,679,914 B1 | 1/2004 | Gabbay |
| 6,692,497 B1 | 2/2004 | Tormala et al. |
| 6,692,498 B1 | 2/2004 | Niiranen et al. |
| 6,702,821 B2 | 3/2004 | Bonutti |
| 6,709,460 B2 | 3/2004 | Merchant |
| 6,712,856 B1 | 3/2004 | Carignan et al. |
| 6,719,794 B2 | 4/2004 | Gerber |
| 6,752,831 B2 | 6/2004 | Sybert et al. |
| 6,770,078 B2 | 8/2004 | Bonutti |
| 6,800,094 B2 | 10/2004 | Burkinshaw |
| 6,814,757 B2 | 11/2004 | Kopylov et al. |
| 6,824,567 B2 | 11/2004 | Tornier et al. |
| 6,852,125 B2 | 2/2005 | Simon et al. |
| 6,852,330 B2 | 2/2005 | Bowman et al. |
| 6,854,330 B2 | 2/2005 | Potter |

(56) References Cited

U.S. PATENT DOCUMENTS

| | | |
|---|---|---|
| 6,855,150 B1 | 2/2005 | Linehan |
| 6,866,684 B2 | 3/2005 | Fell et al. |
| 6,884,242 B2 | 4/2005 | LeHuec et al. |
| 6,890,358 B2 | 5/2005 | Ball et al. |
| 6,893,463 B2 | 5/2005 | Fell et al. |
| 6,896,702 B2 | 5/2005 | Collazo |
| 6,905,513 B1 | 6/2005 | Metzger |
| 6,911,044 B2 | 6/2005 | Fell et al. |
| 6,916,341 B2 | 7/2005 | Rolston |
| 6,926,739 B1 | 8/2005 | O'Connor et al. |
| 6,966,910 B2 | 11/2005 | Ritland |
| 6,966,928 B2 | 11/2005 | Fell et al. |
| 6,972,020 B1 | 12/2005 | Grayson et al. |
| 6,974,480 B2 | 12/2005 | Messerli et al. |
| 6,994,730 B2 | 2/2006 | Posner |
| 6,997,940 B2 | 2/2006 | Bonutti |
| 7,004,971 B2 | 2/2006 | Serhan et al. |
| 7,008,452 B2 | 3/2006 | Hawkins |
| 7,011,687 B2 | 3/2006 | Deffenbaugh et al. |
| 7,018,418 B2 | 3/2006 | Amrich et al. |
| 7,025,790 B2 | 4/2006 | Parks et al. |
| 7,029,475 B2 | 4/2006 | Pajabi |
| 7,060,073 B2 | 6/2006 | Frey et al. |
| 7,105,025 B2 | 9/2006 | Castro et al. |
| 7,105,027 B2 | 9/2006 | Lipman et al. |
| 7,124,762 B2 | 10/2006 | Carter et al. |
| 7,128,744 B2 | 10/2006 | Weaver et al. |
| 7,141,073 B2 | 11/2006 | May et al. |
| 7,160,333 B2 | 1/2007 | Plouhar et al. |
| 7,163,563 B2 | 1/2007 | Schwartz et al. |
| 7,182,787 B2 | 2/2007 | Hassler et al. |
| 7,188,626 B2 | 3/2007 | Foley et al. |
| 7,201,728 B2 | 4/2007 | Sterling |
| 7,223,292 B2 | 5/2007 | Messerli et al. |
| 7,226,482 B2 | 6/2007 | Messerli et al. |
| 7,226,483 B2 | 6/2007 | Gerber et al. |
| 7,235,077 B1 | 6/2007 | Wang et al. |
| 7,235,102 B2 | 6/2007 | Ferree et al. |
| 7,238,203 B2 | 7/2007 | Bagga et al. |
| 7,241,298 B2 | 7/2007 | Nemec et al. |
| 7,247,157 B2 | 7/2007 | Prager et al. |
| 7,252,670 B2 | 8/2007 | Morrison et al. |
| 7,261,739 B2 | 8/2007 | Ralph et al. |
| 7,273,481 B2 | 9/2007 | Lombardo et al. |
| 7,276,070 B2 | 10/2007 | Muckter |
| 7,282,065 B2 | 10/2007 | Kirschman |
| 7,285,134 B2 | 10/2007 | Berry et al. |
| 7,288,094 B2 | 10/2007 | Lindemann et al. |
| 7,288,095 B2 | 10/2007 | Baynham et al. |
| 7,291,150 B2 | 11/2007 | Graf |
| 7,291,169 B2 | 11/2007 | Hodorek |
| 7,297,161 B2 | 11/2007 | Fell |
| 7,306,605 B2 | 12/2007 | Ross |
| 7,322,983 B2 | 1/2008 | Harris |
| 7,322,984 B2 | 1/2008 | Doubler et al. |
| 7,323,012 B1 | 1/2008 | Stone et al. |
| 7,341,589 B2 | 3/2008 | Weaver et al. |
| 7,341,590 B2 | 3/2008 | Ferree |
| 7,341,602 B2 | 3/2008 | Fell et al. |
| 7,361,196 B2 | 4/2008 | Fallin et al. |
| 7,476,225 B2 | 1/2009 | Cole |
| 7,479,160 B2 | 1/2009 | Branch et al. |
| 7,485,147 B2 | 2/2009 | Pappas et al. |
| 7,500,991 B2 | 3/2009 | Bartish, Jr. et al. |
| 7,534,270 B2 | 5/2009 | Ball |
| 7,544,210 B2 | 6/2009 | Schaefer et al. |
| 7,553,331 B2 | 6/2009 | Manspeizer |
| 7,572,291 B2 | 8/2009 | Gil et al. |
| 7,611,540 B2 | 11/2009 | Clifford et al. |
| 7,618,454 B2 | 11/2009 | Bentley et al. |
| 7,632,310 B2 | 12/2009 | Clifford et al. |
| 7,632,311 B2 | 12/2009 | Seedhom et al. |
| 7,637,953 B2 | 12/2009 | Branch et al. |
| 7,641,689 B2 | 1/2010 | Fell et al. |
| 7,655,029 B2 | 2/2010 | Niederberger et al. |
| 7,655,041 B2 | 2/2010 | Clifford et al. |
| 7,678,147 B2 | 3/2010 | Clifford et al. |
| 7,722,676 B2 | 5/2010 | Hanson et al. |
| 7,723,395 B2 | 5/2010 | Ringeisen et al. |
| 7,726,319 B1 | 6/2010 | Boyce |
| 7,744,638 B2 | 6/2010 | Orbay |
| 7,749,276 B2 | 7/2010 | Fitz |
| 7,758,651 B2 | 7/2010 | Chauhan et al. |
| 7,780,670 B2 | 8/2010 | Bonutti |
| 7,806,898 B2 | 10/2010 | Justin et al. |
| 7,819,918 B2 | 10/2010 | Malaviya et al. |
| 7,828,852 B2 | 11/2010 | Bonutti |
| 7,846,211 B2 | 12/2010 | Clifford et al. |
| 7,875,082 B2 | 1/2011 | Naidu |
| 7,879,105 B2 | 2/2011 | Schmieding et al. |
| 7,896,921 B2 | 3/2011 | Smith et al. |
| 7,896,923 B2 | 3/2011 | Blackwell et al. |
| 7,951,176 B2 | 5/2011 | Grady, Jr. et al. |
| 7,959,675 B2 | 6/2011 | Gately |
| 7,967,863 B2 | 6/2011 | Frey et al. |
| 7,972,383 B2 | 7/2011 | Goldstein et al. |
| 7,993,402 B2 | 8/2011 | Sidler |
| 8,002,833 B2 | 8/2011 | Fabris Monterumici et al. |
| 8,002,837 B2 | 8/2011 | Stream et al. |
| 8,002,841 B2 | 8/2011 | Hasselman |
| 8,034,117 B2 | 10/2011 | Matsuzaki et al. |
| 8,043,375 B2 | 10/2011 | Strzepa et al. |
| 8,043,380 B1 | 10/2011 | Park et al. |
| 8,052,753 B2 | 11/2011 | Melvin |
| 8,052,755 B2 | 11/2011 | Naidu |
| 8,083,746 B2 | 12/2011 | Novak |
| 8,088,166 B2 | 1/2012 | Makower et al. |
| 8,088,168 B2 | 1/2012 | Hassler et al. |
| 8,092,530 B2 | 1/2012 | Strzepa et al. |
| 8,092,544 B2 | 1/2012 | Wright et al. |
| 8,100,967 B2 | 1/2012 | Makower et al. |
| 8,114,156 B2 | 2/2012 | Hatch |
| 8,123,805 B2 | 2/2012 | Makower et al. |
| 8,128,697 B2 | 3/2012 | Fell et al. |
| 8,128,704 B2 | 3/2012 | Brown et al. |
| 8,142,503 B2 | 3/2012 | Malone |
| 8,257,444 B2 | 9/2012 | Linares |
| 8,262,707 B2 | 9/2012 | Huebner et al. |
| 8,267,972 B1 | 9/2012 | Gehlert |
| 8,328,805 B2 | 12/2012 | Cole |
| 8,372,078 B2 | 2/2013 | Collazo |
| 8,382,807 B2 | 2/2013 | Austin et al. |
| 8,523,921 B2 | 9/2013 | Horan et al. |
| 8,523,948 B2 | 9/2013 | Slone et al. |
| 8,597,362 B2 | 12/2013 | Shenoy et al. |
| 8,845,724 B2 | 9/2014 | Shenoy et al. |
| 2001/0020143 A1 | 9/2001 | Stark et al. |
| 2001/0023371 A1 | 9/2001 | Bonutti |
| 2001/0037155 A1 | 11/2001 | Merchant |
| 2002/0013587 A1 | 1/2002 | Winquist et al. |
| 2002/0029045 A1 | 3/2002 | Bonutti |
| 2002/0029084 A1 | 3/2002 | Paul et al. |
| 2002/0052606 A1 | 5/2002 | Bonutti |
| 2002/0065560 A1 | 5/2002 | Varga et al. |
| 2002/0091447 A1 | 7/2002 | Shimp et al. |
| 2002/0095154 A1 | 7/2002 | Atkinson et al. |
| 2002/0107574 A1 | 8/2002 | Boehm, Jr. et al. |
| 2002/0133230 A1 | 9/2002 | Repicci |
| 2002/0151978 A1 | 10/2002 | Zacouto et al. |
| 2002/0165550 A1 | 11/2002 | Frey et al. |
| 2003/0055500 A1 | 3/2003 | Fell et al. |
| 2003/0083751 A1 | 5/2003 | Tornier |
| 2003/0088315 A1 | 5/2003 | Supinski |
| 2003/0100950 A1 | 5/2003 | Moret |
| 2003/0109928 A1 | 6/2003 | Pasquet et al. |
| 2003/0120344 A1 | 6/2003 | Michelson |
| 2003/0120346 A1 | 6/2003 | Mercinek et al. |
| 2003/0125807 A1 | 7/2003 | Lambrecht et al. |
| 2003/0139813 A1 | 7/2003 | Messerli et al. |
| 2003/0204265 A1 | 10/2003 | Short et al. |
| 2003/0216809 A1 | 11/2003 | Ferguson |
| 2004/0054409 A1 | 3/2004 | Harris |
| 2004/0117020 A1 | 6/2004 | Frey et al. |
| 2004/0127990 A1 | 7/2004 | Bartish, Jr. et al. |

(56) References Cited

U.S. PATENT DOCUMENTS

| | | |
|---|---|---|
| 2004/0133278 A1 | 7/2004 | Marino et al. |
| 2004/0143336 A1 | 7/2004 | Burkinshaw |
| 2004/0143338 A1 | 7/2004 | Burkinshaw |
| 2004/0148026 A1 | 7/2004 | Bonutti |
| 2004/0167630 A1 | 8/2004 | Rolston |
| 2004/0172133 A1 | 9/2004 | Gerber et al. |
| 2004/0186585 A1 | 9/2004 | Feiwell |
| 2004/0215195 A1 | 10/2004 | Shipp et al. |
| 2004/0230303 A1 | 11/2004 | Gomes et al. |
| 2004/0230315 A1 | 11/2004 | Ek |
| 2004/0236428 A1 | 11/2004 | Burkinshaw et al. |
| 2004/0243240 A1 | 12/2004 | Beaurain et al. |
| 2004/0260302 A1 | 12/2004 | Manspeizer |
| 2004/0267179 A1 | 12/2004 | Lerman |
| 2005/0004671 A1 | 1/2005 | Ross et al. |
| 2005/0027360 A1 | 2/2005 | Webb et al. |
| 2005/0033424 A1 | 2/2005 | Fell |
| 2005/0033426 A1 | 2/2005 | Ogilvie et al. |
| 2005/0043808 A1 | 2/2005 | Felt et al. |
| 2005/0049708 A1 | 3/2005 | Atkinson et al. |
| 2005/0049711 A1 | 3/2005 | Ball |
| 2005/0085815 A1 | 4/2005 | Harms et al. |
| 2005/0119664 A1 | 6/2005 | Carignan et al. |
| 2005/0119744 A1 | 6/2005 | Buskirk et al. |
| 2005/0137708 A1 | 6/2005 | Clark |
| 2005/0143822 A1 | 6/2005 | Paul |
| 2005/0143830 A1 | 6/2005 | Marcinek et al. |
| 2005/0154390 A1 | 7/2005 | Biedermann et al. |
| 2005/0192674 A1 | 9/2005 | Ferree |
| 2005/0222685 A1 | 10/2005 | Hayden et al. |
| 2005/0251080 A1 | 11/2005 | Hyde, Jr. |
| 2005/0261680 A1 | 11/2005 | Draper |
| 2005/0261767 A1 | 11/2005 | Anderson et al. |
| 2005/0267584 A1 | 12/2005 | Burdulis, Jr. et al. |
| 2005/0273114 A1 | 12/2005 | Novak |
| 2005/0288788 A1 | 12/2005 | Dougherty-Shah |
| 2006/0036321 A1 | 2/2006 | Henninger et al. |
| 2006/0064169 A1 | 3/2006 | Ferree |
| 2006/0074423 A1 | 4/2006 | Alleyne |
| 2006/0074492 A1 | 4/2006 | Frey |
| 2006/0085069 A1* | 4/2006 | Kim ........................... 623/17.11 |
| 2006/0100715 A1 | 5/2006 | De Villiers |
| 2006/0106460 A1 | 5/2006 | Messerli et al. |
| 2006/0122620 A1* | 6/2006 | Kim ................................ 606/90 |
| 2006/0129243 A1 | 6/2006 | Wong et al. |
| 2006/0142858 A1 | 6/2006 | Colleran et al. |
| 2006/0149274 A1 | 7/2006 | Justin et al. |
| 2006/0161260 A1 | 7/2006 | Thomas et al. |
| 2006/0178744 A1 | 8/2006 | de Villiers et al. |
| 2006/0235387 A1* | 10/2006 | Peterman ........................ 606/61 |
| 2006/0276907 A1 | 12/2006 | Boyer, II et al. |
| 2007/0027547 A1 | 2/2007 | Rydell et al. |
| 2007/0043356 A1 | 2/2007 | Timm et al. |
| 2007/0106299 A1 | 5/2007 | Manspeizer |
| 2007/0129804 A1 | 6/2007 | Bentley et al. |
| 2007/0129809 A1 | 6/2007 | Meridew et al. |
| 2007/0161993 A1 | 7/2007 | Lowery et al. |
| 2007/0168033 A1 | 7/2007 | Kim et al. |
| 2007/0168036 A1 | 7/2007 | Ainsworth et al. |
| 2007/0173946 A1 | 7/2007 | Bonutti |
| 2007/0198088 A1 | 8/2007 | Biedermann et al. |
| 2007/0198091 A1 | 8/2007 | Boyer et al. |
| 2007/0203581 A1 | 8/2007 | Vanaclocha |
| 2007/0208343 A1 | 9/2007 | Magerl et al. |
| 2007/0225820 A1 | 9/2007 | Thomas et al. |
| 2007/0233141 A1 | 10/2007 | Park et al. |
| 2007/0244483 A9 | 10/2007 | Winslow et al. |
| 2007/0244488 A1 | 10/2007 | Metzger et al. |
| 2007/0265708 A1 | 11/2007 | Brown et al. |
| 2007/0288014 A1 | 12/2007 | Shadduck et al. |
| 2007/0293947 A1 | 12/2007 | Mansmann |
| 2007/0299528 A9 | 12/2007 | Lotke |
| 2008/0015591 A1 | 1/2008 | Castaneda et al. |
| 2008/0015592 A1 | 1/2008 | Long et al. |
| 2008/0015593 A1 | 1/2008 | Pfefferie et al. |
| 2008/0015603 A1 | 1/2008 | Collazo |
| 2008/0015604 A1 | 1/2008 | Collazo |
| 2008/0021566 A1 | 1/2008 | Peters et al. |
| 2008/0033552 A1* | 2/2008 | Lee et al. ................... 623/17.11 |
| 2008/0044449 A1 | 2/2008 | McKay |
| 2008/0071373 A1 | 3/2008 | Molz et al. |
| 2008/0071375 A1 | 3/2008 | Carver et al. |
| 2008/0091270 A1 | 4/2008 | Miller et al. |
| 2008/0097434 A1 | 4/2008 | Moumene et al. |
| 2008/0097441 A1 | 4/2008 | Hayes et al. |
| 2008/0097617 A1 | 4/2008 | Fellinger et al. |
| 2008/0114357 A1* | 5/2008 | Allard et al. .................... 606/61 |
| 2008/0132954 A1 | 6/2008 | Sekhon et al. |
| 2008/0140094 A1 | 6/2008 | Schwartz et al. |
| 2008/0140213 A1 | 6/2008 | Ammann et al. |
| 2008/0154311 A1 | 6/2008 | Staeubli |
| 2008/0154371 A1 | 6/2008 | Fell et al. |
| 2008/0154378 A1 | 6/2008 | Pelo |
| 2008/0161815 A1 | 7/2008 | Schoenefeld et al. |
| 2008/0161933 A1 | 7/2008 | Grotz et al. |
| 2008/0195099 A1 | 8/2008 | Minas |
| 2008/0200995 A1 | 8/2008 | Sidebotham |
| 2008/0234686 A1 | 9/2008 | Beaurain et al. |
| 2008/0262618 A1 | 10/2008 | Hermsen et al. |
| 2008/0275509 A1 | 11/2008 | Clifford et al. |
| 2008/0275552 A1 | 11/2008 | Makower et al. |
| 2008/0275555 A1 | 11/2008 | Makower et al. |
| 2008/0275556 A1 | 11/2008 | Makower et al. |
| 2008/0275557 A1 | 11/2008 | Makower et al. |
| 2008/0275558 A1 | 11/2008 | Clifford et al. |
| 2008/0275559 A1 | 11/2008 | Makower et al. |
| 2008/0275560 A1 | 11/2008 | Clifford et al. |
| 2008/0275561 A1 | 11/2008 | Clifford et al. |
| 2008/0275562 A1 | 11/2008 | Clifford et al. |
| 2008/0275563 A1 | 11/2008 | Makower et al. |
| 2008/0275564 A1 | 11/2008 | Makower et al. |
| 2008/0275565 A1 | 11/2008 | Makower et al. |
| 2008/0275567 A1 | 11/2008 | Makower et al. |
| 2008/0275571 A1 | 11/2008 | Clifford et al. |
| 2008/0281422 A1 | 11/2008 | Schmieding |
| 2008/0281425 A1 | 11/2008 | Thalgott et al. |
| 2009/0012615 A1 | 1/2009 | Fell |
| 2009/0014016 A1 | 1/2009 | Clifford et al. |
| 2009/0018656 A1 | 1/2009 | Clifford et al. |
| 2009/0018665 A1 | 1/2009 | Clifford et al. |
| 2009/0036893 A1 | 2/2009 | Kartalian et al. |
| 2009/0048683 A1 | 2/2009 | Morris |
| 2009/0088763 A1 | 4/2009 | Aram et al. |
| 2009/0088846 A1 | 4/2009 | Myung et al. |
| 2009/0112268 A1 | 4/2009 | Cole |
| 2009/0118830 A1 | 5/2009 | Fell |
| 2009/0164014 A1 | 6/2009 | Liljensten et al. |
| 2009/0182433 A1 | 7/2009 | Reiley et al. |
| 2009/0198341 A1 | 8/2009 | Choi et al. |
| 2009/0210063 A1 | 8/2009 | Barrett |
| 2009/0226068 A1 | 9/2009 | Fitz et al. |
| 2009/0248026 A1 | 10/2009 | Draper |
| 2009/0259311 A1 | 10/2009 | Shterling et al. |
| 2009/0259312 A1 | 10/2009 | Shterling et al. |
| 2009/0306783 A1 | 12/2009 | Blum |
| 2009/0312807 A1 | 12/2009 | Boudreault et al. |
| 2009/0318924 A1 | 12/2009 | Helenbolt et al. |
| 2009/0318976 A1 | 12/2009 | Gabriel et al. |
| 2010/0023126 A1 | 1/2010 | Grotz |
| 2010/0049322 A1 | 2/2010 | McKay |
| 2010/0049325 A1 | 2/2010 | Biedermann et al. |
| 2010/0057216 A1 | 3/2010 | Gannoe et al. |
| 2010/0076564 A1 | 3/2010 | Schilling et al. |
| 2010/0106247 A1 | 4/2010 | Makower et al. |
| 2010/0106248 A1 | 4/2010 | Makower et al. |
| 2010/0114322 A1 | 5/2010 | Clifford et al. |
| 2010/0121355 A1 | 5/2010 | Gittings et al. |
| 2010/0121457 A1 | 5/2010 | Clifford et al. |
| 2010/0125266 A1 | 5/2010 | Deem et al. |
| 2010/0131068 A1 | 5/2010 | Brown et al. |
| 2010/0131069 A1 | 5/2010 | Halbrecht |
| 2010/0137996 A1 | 6/2010 | Clifford et al. |
| 2010/0145449 A1 | 6/2010 | Makower et al. |
| 2010/0161057 A1 | 6/2010 | Berry et al. |

(56) References Cited

U.S. PATENT DOCUMENTS

| | | |
|---|---|---|
| 2010/0168857 A1 | 7/2010 | Hatch |
| 2010/0198354 A1 | 8/2010 | Halbrecht |
| 2010/0204798 A1 | 8/2010 | Gerbec et al. |
| 2010/0262246 A1 | 10/2010 | Attia |
| 2010/0292731 A1 | 11/2010 | Gittings et al. |
| 2010/0292733 A1 | 11/2010 | Hendricksen et al. |
| 2010/0305698 A1 | 12/2010 | Metzger et al. |
| 2010/0305708 A1 | 12/2010 | Lang et al. |
| 2011/0004305 A1 | 1/2011 | Jansson et al. |
| 2011/0054627 A1 | 3/2011 | Bear |
| 2011/0060422 A1 | 3/2011 | Makower et al. |
| 2011/0093073 A1 | 4/2011 | Gatt et al. |
| 2011/0093079 A1 | 4/2011 | Slone et al. |
| 2011/0093080 A1 | 4/2011 | Slone et al. |
| 2011/0121457 A1 | 5/2011 | Clevenger et al. |
| 2011/0137415 A1 | 6/2011 | Clifford et al. |
| 2011/0172768 A1 | 7/2011 | Cragg et al. |
| 2011/0202138 A1 | 8/2011 | Shenoy et al. |
| 2011/0213466 A1 | 9/2011 | Shenoy et al. |
| 2011/0224734 A1 | 9/2011 | Schelling |
| 2011/0230919 A1 | 9/2011 | Alleyne |
| 2011/0238180 A1 | 9/2011 | Fritz et al. |
| 2011/0245928 A1 | 10/2011 | Landry et al. |
| 2011/0264216 A1 | 10/2011 | Makower et al. |
| 2011/0270393 A1 | 11/2011 | Marvel |
| 2011/0288643 A1 | 11/2011 | Linder-Ganz et al. |
| 2012/0022649 A1 | 1/2012 | Robinson et al. |
| 2012/0022655 A1 | 1/2012 | Clifford |
| 2012/0046754 A1 | 2/2012 | Clifford et al. |
| 2012/0053644 A1 | 3/2012 | Landry et al. |
| 2012/0065640 A1 | 3/2012 | Metzger et al. |
| 2012/0116522 A1 | 5/2012 | Makower et al. |
| 2012/0136449 A1 | 5/2012 | Makower et al. |
| 2012/0179273 A1 | 7/2012 | Clifford et al. |
| 2012/0197410 A1 | 8/2012 | Horan et al. |
| 2012/0221106 A1 | 8/2012 | Makower et al. |
| 2012/0271366 A1 | 10/2012 | Katrana et al. |
| 2012/0290088 A1 | 11/2012 | Amirouche et al. |
| 2013/0013066 A1 | 1/2013 | Landry et al. |
| 2013/0013067 A1 | 1/2013 | Landry et al. |
| 2013/0041416 A1 | 2/2013 | Regala et al. |
| 2013/0096629 A1 | 4/2013 | Rollinghoff et al. |
| 2013/0150977 A1 | 6/2013 | Gabriel et al. |
| 2013/0166036 A1 | 6/2013 | De Cortanze et al. |
| 2013/0190886 A1 | 7/2013 | Tepic et al. |
| 2013/0204378 A1 | 8/2013 | Slone et al. |
| 2013/0211521 A1 | 8/2013 | Shenoy et al. |
| 2013/0289728 A1 | 10/2013 | Makower et al. |
| 2013/0304208 A1 | 11/2013 | Clifford et al. |
| 2013/0325123 A1 | 12/2013 | Clifford et al. |
| 2013/0338783 A1 | 12/2013 | Slone et al. |
| 2014/0052266 A1 | 2/2014 | Slone et al. |
| 2014/0156004 A1 | 6/2014 | Shenoy et al. |
| 2014/0156005 A1 | 6/2014 | Shenoy et al. |
| 2014/0257292 A1 | 9/2014 | Embleton et al. |

FOREIGN PATENT DOCUMENTS

| | | |
|---|---|---|
| DE | 19855254 A1 | 6/2000 |
| EP | 0383419 A1 | 8/1990 |
| EP | 0953317 B1 | 4/2004 |
| EP | 1410769 A2 | 4/2004 |
| EP | 1770302 A1 | 4/2007 |
| EP | 1429675 B1 | 10/2007 |
| EP | 1682020 B1 | 10/2007 |
| EP | 1847228 A1 | 10/2007 |
| EP | 1847229 A2 | 10/2007 |
| EP | 1005290 B1 | 2/2008 |
| EP | 1468655 B1 | 5/2008 |
| EP | 2452641 A1 | 5/2012 |
| FR | 2926456 A1 | 7/2009 |
| GB | 1507953 | 4/1978 |
| GB | 2223406 | 4/1990 |
| GB | 2250919 | 10/1993 |
| JP | 59131348 | 7/1984 |
| JP | 7100159 | 4/1995 |
| JP | 2532346 B2 | 11/1996 |
| JP | 2000503865 | 4/2000 |
| JP | 2001145647 | 5/2001 |
| JP | 2003102744 | 4/2003 |
| JP | 2006280951 | 10/2006 |
| JP | 2007167318 | 7/2007 |
| JP | 2007167319 | 7/2007 |
| JP | 2007170969 | 7/2007 |
| NZ | 533300 | 2/2005 |
| RU | 1769868 A1 | 10/1992 |
| RU | 2085148 | 7/1997 |
| RU | 2217105 C2 | 11/2003 |
| RU | 2241400 C2 | 12/2004 |
| SU | 578063 A1 | 10/1977 |
| SU | 578957 A1 | 11/1977 |
| SU | 624613 A1 | 9/1978 |
| SU | 640740 A1 | 1/1979 |
| SU | 704605 A1 | 12/1979 |
| SU | 719612 A1 | 3/1980 |
| SU | 741872 A1 | 6/1980 |
| SU | 1186204 | 10/1985 |
| SU | 1251889 | 8/1986 |
| SU | 1316666 A1 | 6/1987 |
| SU | 1588404 | 8/1990 |
| SU | 1699441 A1 | 12/1991 |
| WO | 91/07137 | 5/1991 |
| WO | 94/06364 A1 | 3/1994 |
| WO | 96/19944 A1 | 7/1996 |
| WO | 2004019831 A2 | 3/2004 |
| WO | 2004024037 A2 | 3/2004 |
| WO | 2006045091 A2 | 4/2006 |
| WO | 2006049993 | 5/2006 |
| WO | 2006110578 A3 | 10/2006 |
| WO | 2007056645 A2 | 5/2007 |
| WO | 2007090009 A1 | 8/2007 |
| WO | 2007090015 A1 | 8/2007 |
| WO | 2007090017 A1 | 8/2007 |
| WO | 2007106962 A1 | 9/2007 |
| WO | 2007109132 A2 | 9/2007 |
| WO | 2007109140 A2 | 9/2007 |
| WO | 2007109417 A2 | 9/2007 |
| WO | 2007109436 A2 | 9/2007 |
| WO | 2007114769 A1 | 10/2007 |
| WO | 2007117571 A2 | 10/2007 |
| WO | 2008006098 A2 | 1/2008 |
| WO | 2009/018365 A1 | 2/2009 |
| WO | 2011025959 A1 | 3/2011 |
| WO | 2012/062908 A1 | 5/2012 |

OTHER PUBLICATIONS

PCT International Search Report and Written Opinion dated Jan. 9, 2014, for related application PCT/US2013/058877 filed Sep. 10, 2013 entitled "Method and Apparatus for Treating Canine Cruciate Ligament Disease," Vivek Shenoy.

Bruce et al., "Patellar Contact Pressure Changes with Anteromedialization of Tibial Tubercle, Lateral Release, and New Technique for Elevating Quadriceps Tendon: A Biomechanical Study," Journal of Surgical Orthopaedic Advances 22(4), pp. 270-276, 2013.

Notice of Allowance dated Feb. 3, 2015, in connection with related U.S. Appl. No. 14/175,813, filed Feb. 7, 2014.

Final Office Action dated Feb. 26, 2015, in connection with related U.S. Appl. No. 13/002,829, filed Jan. 6, 2011.

Lapinskaya, Valentina Spiridonovna, "Treatment of Diseases and Injuries of Hip Joint Using a Method of Distraction", Kuibyshev Medical Institute, 1990.

Larionov D. Yu, et al., "Medical Devices," Scientific and Technical Bimonthy Journal, May-Jun. 2008.

Lapinskaya, V.S., et al., "An Endoapparatus for Restoration of the Hip Joint," Writers Collective, 2008, UDK 615.472.03:616.728.2-089.28; pp. 8-12.

Lentsner, A.A., et al., "Device for Functional Relief of Hip Joint in Cotyloid Cavity Fracture Cases", Ortop Travmatol Protez. Apr. 1990 (4) 44-6.

(56) References Cited

OTHER PUBLICATIONS

Andriacchi, Thomas P., Ph.D. et al.; "Methods for Evaluating the Progression of Osteoarthritis"; Journal of Rehabilitation Research and Development, vol. 37, No. 2., Mar./Apr. 2000, pp. 163-170.
Arendt, Elizabeth, M.D.; "Anatomy and Malalignment of the Patellofemoral Joint—Its Relation to Patellofemoral Arthrosis"; Clinical Orthopaedics and Related Research; 2005, No. 436, pp. 71-75.
Benzel, Edward; "Qualitative Attributes of Spinal Implants"; in: Biomechanics of Spine Stabilization, 1995, pp. 137-150.
Buckwalter, Joseph A.; "Joint Distraction for Osteoarthritis"; The Lancet, Department of Orthopaedic Surgery, University of Iowa Hospitals and Clinics, vol. 347, Feb. 3, 1996, pp. 279-280.
Coathup, M.J. et al.; "Osseo-mechanical induction of extra-cortical plates with reference to their surface properties and gemoetric designs", Elsevier, Biomaterials 20 (1999) pp. 793-800.
Deie, Masataka, M.D. et al.; "A New Articulated Distraction Arthroplasty Device for Treatment of the Osteoarthritic Knee Joint: A Preliminary Report"; Arthroscopy: The Journal of Arthroscopic and Related Surgery; vol. 23, No. 8 Aug. 2007: pp. 833-838.
Dienst, M. et al.; "Dynamic External Fixation for Distal Radius Fractures"; Clinical Orthopaedics and Related Research, 1997, vol. 338, pp. 160-171.
Gunther, Klaus-Peter, M.D.; "Surgical Approaches for Osteoarthritis"; Best Practice & Research Clinical Rheumatology, vol. 15, No. 4, 2001, pp. 627-643.
Hall, J. et al.; "Use of a Hinged External Fixator for Elbow instability after Severe Distal Humeral Fracture"; Journal of Orthopaedic Trauma, 2000, vol. 14, No. 6, pp. 442-448.
Klein, D. et al.; "Percutaneous Treatment of Carpal, Metacarpal, and Phalangeal Injuries"; Clinical Orthopaedics and Related Research, 2000, vol. 375, pp. 116-125.
Krakauer J. et al.; "Hinged Device for Fractures involving the Proximal Interphalangeal Joint"; Clinical Orthopaedics and Related Research, 1996, vol. 327, pp. 29-37.
Leon, Heriberto Ojeda, M.D. et al.; "Minimally Invasive Selective Osteotomy of the Knee: A New Surgical Technique"; Arthroscopy: The Journal of Arthroscopic and Related Surgery, vol. 17, No. 5 May-Jun. 2001: pp. 510-516.
Madey, S. et al.; "Hinged External Fixation of the elbow: optimal axis alignment to minimize motion resistance"; Journal of Orthopaedic Trauma, 2000, vol. 14, No. 1, pp. 41-47.
Neel, Michael D., M.D. et al.; "Early Multicenter Experience With a Noninvasive Expandable Prosthesis"; Clinical Orthopaedics and Related Research, 2003, No. 415, pp. 72-81.
Neel, Michael D., M.D.; "Repiphysis—Limb Salvage System for the Skeletally Immature"; Wright Medical Technology, Reipiphysis Limb Salvage System, 2004, pp. 1-8.
Nockels, Russ P.; "Dynamic Stabilization in the Surgical Management of Painful Lumbar Spinal Disorders"; Spine, 2005, vol. 30, No. 16S, pp. S68-S72.
Orthofix; "Xcaliber Articulated Ankle"; advertising brochure, May 2004.
Orthofix; "Gentle Limb Deformity Correction"; website pages, http://www.eight-plate.com/, 2008.
Perry, Clayton R. et al.; "Patellar Fixation Protected with a Load-Sharing Cable: A Mechanical and Clinical Study"; Journal of Orthopaedic Trauma, 1988, vol. 2, No. 3, pp. 234-240.
Pilliar et al., "Bone Ingrowth and Stress Shielding with a Porous Surface Coated Fracture Fixation Plate," Journal of Biomedical Materials Research, vol. 13, (1979), pp. 799-810.
Repicci, John A., M.D. et al. "Minimally Invasive Unicondylar Knee Arthroplasty for the Treatment of Unicompartmental Osteoarthritis: an outpatient arthritic bypass procedure"; Orthopedic Clinics of North America, 35 (2004), pp. 201-216.
Sharma, Leena et al. "The Mechanism of the Effect of Obesity in Knee Osteoarthritis—The Mediating Role of Malalignment"; Arthritis & Rheumatism, vol. 43, No. 3, Mar. 2000, pp. 568-575.
Sommerkamp, G. et al.; "Dynamic External Fixation of Unstable Fractures of the Distal Part of the Radius"; The Journal of Bone and Joint Surgery; Aug. 1994, vol. 76-A, No. 8, pp. 1149-1161.
Tencer, Allan F. et al. "Fixation of the Patella (Chap. 9.3)"; in: Biomechanics in Orthopedic Trauma Bone Fracture and Fixation, 1994.
Thakur, A.J.; "Tension Band Wiring"; in; The Elements of Fracture Fixation, 1997, pp. 126-146.
Uchikura, C. et al.; "Comparative Study of Nonbridging and Bridging External Fixators from Unstable Distal Radius fractures"; Journal of Orthopaedic Science, 2004, vol. 9, No. 6, pp. 560-565.
Van Der Esch, M. et al.; "Structural Joint Changes, Malalignment, and Laxity in Osteoarthritis of the knee"; Scand J Rheumatol 2005; 34: pp. 298-301.
Weisstein, Jason S., M.D. et al.; "Oncologic Approaches to Pediatric Limb Preservation"; Journal of the American Academy of Orthopaedic Surgeons; vol. 13, No. 8, Dec. 2005, pp. 544-554.
Wilke, Hans-Joachim et al.; "Biomechanical Evaluation of a New Total Posterior-Element Replacement System"; Spine, 2006, vol. 31, No. 24, pp. 2790-2796.
Yamamoto, Ei et al.; "Effects of Stress Shielding on the Transverse Mechanical Properties of Rabbit Patellar Tendons"; Journal of Biomechanical Engineering, 2000, vol. 122, pp. 608-614.
Non-Final Office Action dated Apr. 11, 2014, in connection with related U.S. Appl. No. 14/175,829, filed Feb. 2, 2014, Vivek Shenoy.
Response to First Non-Final Office Action dated May 5, 2014, in connection with related U.S. Appl. No. 14/175,829, filed Feb. 7, 2014, Vivek Shenoy.
Response to Non-Final Office Action dated May 26, 2015, in connection with related U.S. Appl. No. 13/002,829, filed Jan. 6, 2011.
Response to Non-Final Office Action dated Apr. 20, 0215, in connection with related U.S. Appl. No. 13/843,128, filed Mar. 15, 2013.
Final Office Action dated Jun. 10, 2015, in connection with related U.S. Appl. No. 13/843,128, filed Mar. 15, 2013.
Partial International Search dated May 11, 2015, in connection with related PCT/US2015/019938, filed Mar. 11, 2015.
Response to Election/Restriction dated Jul. 1, 2014 in connection with related U.S. Appl. No. 14/175,813, filed Feb. 7, 2014.
Notice of Allowance date mailed Aug. 4, 2014 in connection with related U.S. Appl. No. 14/175,829, filed Feb. 7, 2014, Vivek Shenoy.
Non-Final Rejection Office Action dated Aug. 27, 2014 in connection with related U.S. Appl. No. 14/175,813, filed Feb. 7, 2014, Vivek Shenoy.
Synthes, Inc., LCP Proximal Tibial Plate 3.5; Technique Guide; pp. 1-20; Jun. 2011.
European Search Report dated Aug. 7, 2014, issued in connection with related EP14164658. Applicant received copy Aug. 28, 2014 from foreign associate.
Extended Search Report dated Aug. 26, 2014, issued in connection with related EP14164658.
Restriction Requirement dated Aug. 25, 2014, issued in connection with related U.S. Appl. No. 13/843,128, filed Mar. 15, 2013.
Response to Restriction Requirement dated Oct. 27, 2014, issued in connection with related U.S. Appl. No. 13/843,128, filed Mar. 15, 2013.
PCT International Search Report and Written Opinion dated Oct. 20, 2010, for related application PCT/US2010/046996 filed Aug. 27, 2010 entitled "Method and Apparatus for Force Redistribution in Articular Joints"; Vivek Shenoy, Mark Deem and Hanson Gifford.
Office Action dated May 17, 2012, in connection with related U.S. Appl. No. 13/002,829, filed Jan. 6, 2011, Shenoy.
Office Action dated Jul. 24, 2012, in connection with related U.S. Appl. No. 12/870,462, filed Aug. 27, 2010, Shenoy.
Final (Rejection) Office Action dated Mar. 18, 2013, in connection with related U.S. Appl. No. 12/870,462, filed Aug. 27, 2010.
Final (Rejection) Office Action dated Jan. 31, 2013, in connection with related U.S. Appl. No. 13/002,829, filed Jan. 6, 2011.
Office Action dated Jul. 9, 2012, in connection with related European Application No. 10812664, entitled Method and Apparatus for Force Redistributon in Articular Joints, filed Aug. 27, 2010, Cotera, Inc.

(56) References Cited

OTHER PUBLICATIONS

Maquet, P., Biomechanical Treatment of Patellofemoral Osteoarthritis. Advancement of the Patellar Tendon; Review of Rheumatism and Osteoarticular Diseases, National Library of Medicine, Dec. 1963, vol. 30, Issue 12, pp. 780-785.

Maquet, Paul G.J., Biomechanics of the Knee With Application to the Pathogenesis and the Surgical Treatment of Osteoarthritis; Springer-Verlag Berlin Heidelberg New York, 1976, pp. 134-204.

Sridhar et al., Obesity and symptomatic osteoarthritis of the knee, The Journal of Bone & Joint Surgery, Instructional Review, vol. 94-B, No. 4, Apr. 2012, pp. 433-441.

Lasmar, et al., Importance of the Different Posterolateral Knee Static Stabilizers: Biomechanical Study; Clinics 2010; 65(4) pp. 433-440.

Hunter, David et al., Alignment and Osteoarthritis of the Knee, Journal of Bone and Joint Surgery, 2009: 91 Suppl. 1:85-9, pp. 85-89.

Halbrecht, Jeffrey L., Arthroscopic Patella Realignment: An All-Inside Technique, Arthroscopy: The Journal of Arthroscopic and Related Surgery, vol. 17, No. 9 Nov.-Dec. 2001; pp. 940-945.

Arnold, Allison S., et al., Do the hamstrings operate at increased muscle-tendon lengths and velocities after surgical lengthening? Journal of Biomechanics, Mar. 2005; pp. 1-9.

Unnanuntana, Aasis et al., Management of chronic lateral instability due to lateral collateral ligament deficiency after total knee arthroplasty: a case report; Journal of Medical Case Reports, 2010, 4:144; pp. 1-5.

Maquet, P., Biomechanical Aspects of the Relationship between Femur and Patella, Z. Orthop. 112 (1974); pp. 620-623.

Kwak, et al., Hamstrings and Iliotibial Band Forces Affect Knee Kinematics and Contact Pattern, Journal of Orthopaedic Research, 18: 101-108; The Journal of Bone and Joint Surgery, Inc. 1999.

Maquet P., Reduction of the articular pressure of the hip by surgical lateralization of the greater trochanter, PMID: 1015273, Clin Orthop Relat Res. Mar.-Apr. 1977; (123): 138 (Abstract only).

Maquet P., Importance of the position of the greater trochanter, PMID: 2382566, Acta Orthop Belg. 1990; 56 (1 Pt. B): 307 (Abstract only).

Maquet, Paul, "Advancement of the Tibial Tubersosity," Clinical Orthopaedics and Related Research, No. 15, 1976, pp, 225-230.

Townsend et al., "The Biomechanics of the Human Patella and its Implications for Chodromalacia," Journal of Biomechanics, 1977, vol. 10, pp. 403-407.

Supplementary European Search Report dated May 23, 2012 for related application EP10812664 filed Aug. 27, 2010, entitled "Method and Apparatus for Force Redistribution in Articular," Cotera, Inc.

Arnoczky et al., Biomechanical Analysis of Forces Acting About the Canine Hip, American Journal Veterinary Research, vol. 42, Issue: 9, Sep. 1981, pp. 1581-1585.

Becker et al., Surgical Treatment of Isolated Patellofemoral Osteoarthritis, Clinical Orthopaedics and Related Research vol. 466, No. 2, Feb. 2008, pp. 443-449.

Cerejo et al., The Influence of Alignment on Risk of Knee Osteoarthritis Progression According to Baseline Stage of Disease, Arthritis & Rheumatism, vol. 46, No. 10, Oct. 2002, pp. 2632-2636.

Clifford et al., The KineSpring load absorber implant: Rationale, Design and Biomechanical Characterization, Journal of Medical Engineering & Technology, vol. 35, No. 1, Jan. 2011, pp. 65-71.

Delp et al., An Interactive Graphics-Based Model of the Lower Extremity to Study Orthopaedic Surgical Procedures, IEEE Transactions on Biomedical Engineering, vol. 37, No. 8, Aug. 1990, pp. 757-767.

Delp et al., Biomechanical Analysis of the Chiari Pelvic Osteotomy Preserving Hip Abductor Strength, Reprinted from Clinical Orthopaedics, vol. 25, May 1990, pp. 189-198.

Free et al, Trochanteric Transfer in Total Hip Replacement: Effects on the Moment Arms and Force-Generating Capacities of the Hip Abductors, Journal of Orthopaedic Research, vol. 14, No. 2, 1996, pp. 245-250.

Jack Farr, M.D., Tibial Tubercle Osteotomy, Techniques in Knee Surgery, vol. 2, Issue 1, 2003, pp. 28-42.

Goetz et al., Hip Joint Contact Force in the Emu (*Dromaius novaehollandiae*) during Normal Level Walking, Journal of Biomechanics, 41(4), 2008, pp. 770-778.

Jacobsen et al., Hip dysplasia: a significant risk factor for the development of hip osteoarthritis. A cross-sectional survey, Rheumatology vol. 44 No. 2, 2005, pp. 211-218.

Jingushi et al., Transtrochanteric Valgus Osteotomy for the Treatment of Osteoarthritis of the Hip Secondary to Acetabular Dysplasia, The Journal of Bone & Joint Surgery [Br], vol. 84-B, No. 4, May 2002, pp. 535-539.

Kirkley et al., The Effect of Bracing on Varus Gonarthrosis, The Journal of Bone and Joint Surgery, vol. 81-A, No. 4, Apr. 1999, pp. 539-548.

Lafeber et al., Unloading Joints to Treat Osteoarthritis, including Joint Distraction, Current Opinion in Rheumatology 2006, 18, pp. 519-525.

Lloyd et al., An EMG-driven Musculoskeletal Model to Estimate Muscle Forces and Knee Joint Moments in Vivo, Journal of Biomechanics 36, 2003, pp. 765-776.

Lloyd et al., Strategies of Muscular Support of Varus Andvalgus Isometric Loads at the Human Knee, Journal of Biomechanics 34, 2001, pp. 1257-1267.

Maquet, P, Biomechanics of Hip Dysplasia, Acta Ortopaedica Belgica, vol. 65-3, 1999, pp. 302-314.

McWilliams et al., Mild Acetabular Dysplasia and Risk of Osteoarthritis of the hip: a case-control study, Annals of the Rheumatic Diseases, 2010; 69, pp. 1774-1778.

Merritt et al., Influence of Muscle-Tendon Wrapping on Calculations of Joint Reaction Forces in the Equine Distal Forelimb, Journal of Biomedicine and Biotechnology, vol. 2008, Article ID 165730, 9 pages.

Pedersen et al., A Model to Predict Canine Pelvic Limb Musuloskeletal Geometry, Acta Anat 1991; 140, pp. 139-145.

Pollo et al., Knee Bracing for Unicompartmental Osteoarthritis, Journal of the American Academy of Orthopaedic Surgeons, vol. 14, No. 1, Jan. 2006, pp. 5-11.

Pollo et al., Reduction of Medial Compartment Loads with Valgus Bracing of the Osteoarthritic Knee, The American Journal of Sports Medicine, vol. 30, No. 3, 2002, pp. 414-421.

Saleh et al., Operative Treatment of Patellofemoral Arthritis, The Journal of Bone & Joint Surgery, vol. 87-A, No. 3, Mar. 2005, pp. 659-671.

Sharma et al., The Role of Knee Alignment in Disease Progression and Functional Decline in Knee Osteoarthritis, JAMA, vol. 286, No. 2, Jul. 11, 2001, pp. 188-195.

Sims et al., Investigation of Hip Abductor Activation in Subjects with Clinical Unilateral Hip Osteoarthritis, Annals of the Rheumatic Diseases, 2002; 61: pp. 687-692.

Thorp et al., The biomechanical effects of focused muscle training on medial knee loads in OA of the knee: a pilot, proof of concept study, Journal of Musculoskeletal and Neuronal Interactions, 10(2): 2010, pp. 166-173.

Wenger et al., Early Surgical Correction of Residual Hip Dysplasia: The San Diego Children's Hospital Approach, Acta Orthopaedica Belgica, vol. 65, 1999, pp. 277-287.

Winby et al., Muscle and External Load Contribution to Knee Joint Contact Loads during Normal Gait, Journal of Biomechanics 42, 2009, pp. 2294-2300.

Response to Final Office Action dated Apr. 1, 2013, in connection with related U.S. Appl. No. 13/002,829 International filing date Aug. 27, 2010.

Amendment and Response to Final Office Action dated May 20, 2013, in connection with related U.S. Appl. No. 12/870,462, filed Aug. 27, 2010.

Advisory Action dated Apr. 23, 2013 in connection with related U.S. Appl. No. 13/002,829, filed Jan. 6, 2011.

Advisory Action dated Jun. 20, 2013 in connection with related U.S. Appl. No. 13/002,829, filed Jan. 6, 2011.

Tew, M et al.; Anteriorization of the quadriceps tendon. A biomechanical study on a new technique for unloading the patel-

(56) References Cited

OTHER PUBLICATIONS lofemoral joint. University of Tennessee College of Medicine; Poster No. 0848 • ORS 2012 Annual Meeting.
Miller, R.K., Goodfellow, J.W., Murray, D.W. and O'Connor, J.J., In vitro measurement of patellofemoral force after three types of knee replacement; The Journal of Bone & Joint Surgery (Br), vol. 80-B, No. 5, Sep. 1998; pp. 900-906.
Ganesh, V.K., et al., Biomechanics of bone-fracture fixation by stiffness-graded plates in comparison with stainless-steel plates, Biomedical Engineering Online, 2005, 4:46, 15 pgs.
Benli, Semih et al., Evaluation of bone plate with low-stiffness material in terms of stress distribution, Journal of Biomechanics, 41 (2008) 3229-3235.
Haase, Kristina et al., A Discussion on Plating Factors that Affect Stress Shielding Using Finite Element Analysis, Journal of Biomechanical Science and Engineering, vol. 5, No. 2, 2010, pp. 129-.
Anatomic Locked Plating System Brochure, BIOMET® Orthopedics, Form BMET0002.0, REV 053112, pp. 1-16, Copyright 2012.
SPS Periarticular Plates Brochure, STRYKER® Trauma AG, Literature No. 982274, Lot B46404, pp. 1-8; Copyright 2004.
Zimmer® Periarticular Distal Femoral Locking Plate Surgical Technique, the Science of the Landscape, Zimmer, 97-2347-044-00 Rev. 1 7.5 ML; pp. 1-20; Copyright 2005.
Hessmann et al., Compression Plate With or Without Lag Screw; AO Surgery Reference—Online reference in clinical life; Distal Tibia—Reduction & Fixation—Compression Plate; https://www2.aofoundation.org/wps/portal; pp. 1-9; Dec. 3, 2008.
LCP Locking Compression Plate—Ordering Information; Synthes@, 036.000.017, SE_042064 AD, 31080015; pp. 1-68; Copyright 2008.
Plates for 4.5 mm and 6.5 mm Screws; Raj Surgical Works; http://www.orthoindustries.com/plates-for-4-5-mm-and-6-5-mm-screws.html; pp. 1-8; printed Nov. 19, 2012.
Final Office Action dated Jan. 31, 2013, in connection with related U.S. Appl. No. 13/002,829, filed Jan. 6, 2011.
Gumpel et al., An Objective Assessment of Synovitis of the Knee: Measurement of the Size of the Suprapatellar Pouch on Xeroradiography. Annals of the Rheumatic Diseases. 1980, (39): 359-366.
Response to First Non-Final Office Action dated Jan. 25, 2016, in connection with related U.S. Appl. No. 14/642,121, filed Mar. 9, 2015.
Appellant's Brief dated Mar. 15, 2016, in connection with related U.S. Appl. No. 13/002,829, filed Jan. 6, 2011.
International Search Report and Written Opinion dated Jul. 3, 2015, in connection with related PCT/US2015/019938, filed Mar. 11, 2015.
Restriction Requirement dated Jul. 23, 2015, in connection with related U.S. Appl. No. 14/642,121, filed Mar. 9, 2015.
Restriction Requirement dated Jul. 22, 2015, in connection with related U.S. Appl. No. 14/644,792, filed Mar. 11, 2015.
Response to Final Office Action dated Aug. 10, 2015, in connection with related U.S. Appl. No. 13/843,128, filed Mar. 15, 2013.
Response to Restriction Requirement dated Sep. 23, 2015, in connection with related U.S. Appl. No. 14/642,121, filed Mar. 9, 2015.
Response to Restriction Requirement dated Sep. 11, 2015, in connection with related U.S. Appl. No. 14/644,792, filed Mar. 11, 2015.
Supplemental Response to Final Office Action dated Sep. 3, 2015, in connection with related U.S. Appl. No. 13/843,128, filed Mar. 15, 2013.
Final Office Action dated Sep. 51, 2015, in connection with related U.S. Appl. No. 13/002,829, filed Jan. 6, 2011.
Non-final Office Action dated Sep. 25, 2015, in connection with related U.S. Appl. No. 14/644,792, filed Mar. 11, 2015.
Chow, S. P. et al., Fracture of the Tibial Tubercle in the Adolescent; British Editorial Society of Bone and Joint Surgery, vol. 72-B. No. 2, Mar. 1990.
Non-Final Office Action dated Oct. 7, 2015, in connection with U.S. Appl. No. 14/642,121, filed Mar. 9, 2015.

\* cited by examiner

METHOD AND APPARATUS FOR ALTERING BIOMECHANICS OF THE SPINE
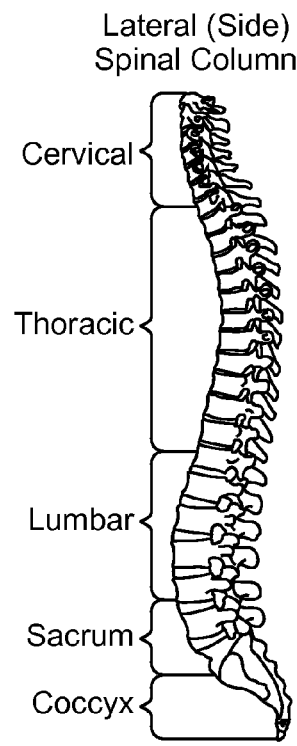
FIG. 1
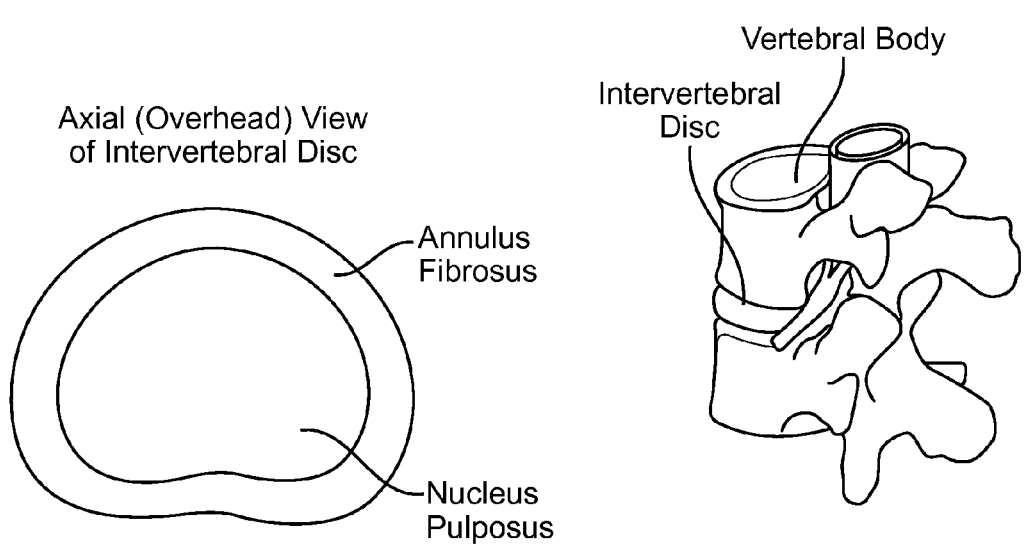
FIG. 2A
FIG. 2B

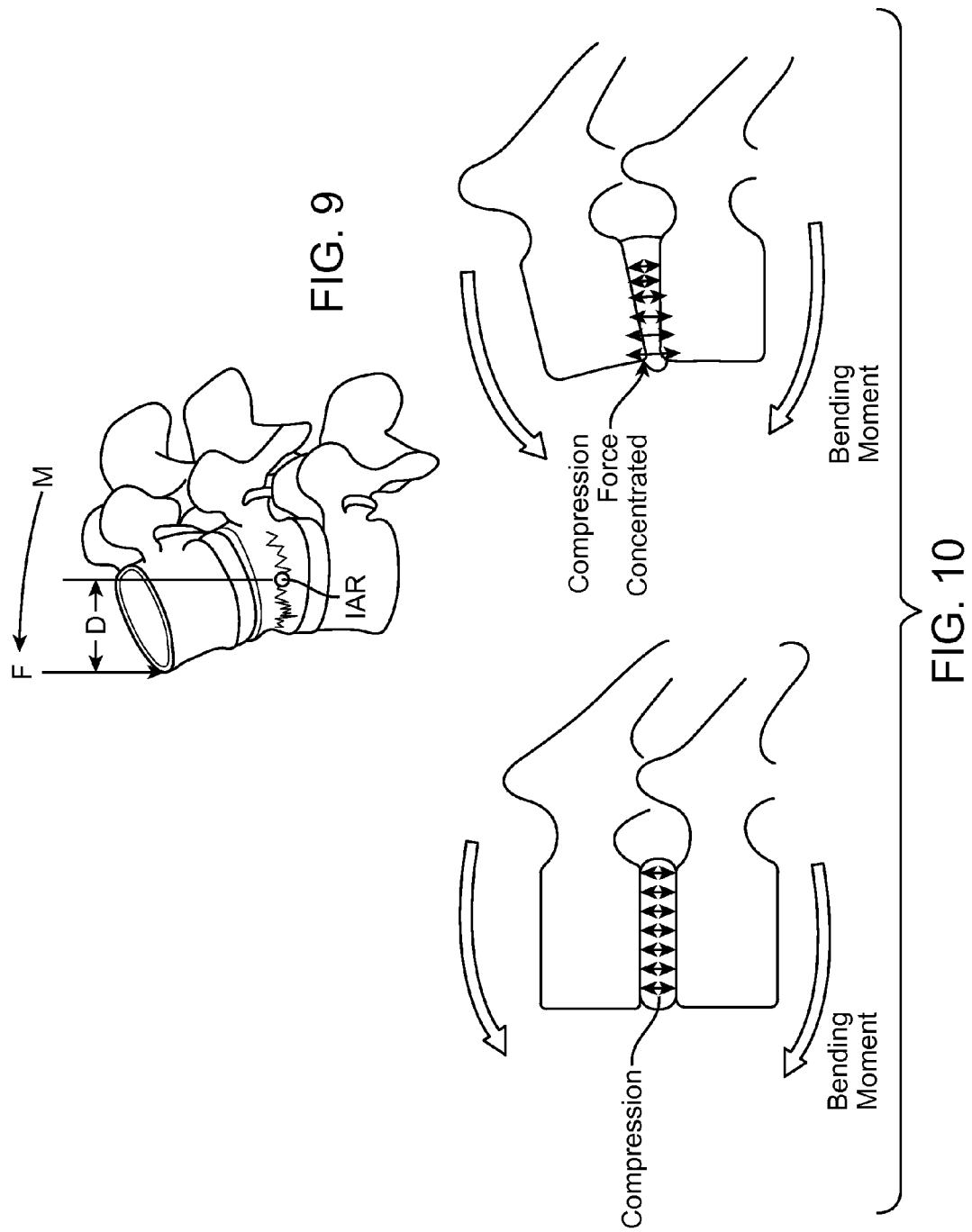

METHOD AND APPARATUS FOR ALTERING BIOMECHANICS OF THE SPINE

FIELD OF THE INVENTION

The present invention generally relates to the field of orthopedics. In particular, the present invention is directed to an interventional technique and an implant for altering biomechanics of the spine to provide a therapeutic effect.

BACKGROUND

Spinal disorders are a major cause of disability, both in the younger and aged population. In the young population, there is association between strenuous work like lifting and lumbar disc problems. In the aging population, osteoporosis of the vertebral bodies can result in vertebral compression fractures.

The spinal column consists of individual bones called vertebrae. These vertebrae are connected with soft cartilaginous disks between each vertebrae called intervertebral discs. From a lateral view, the spine has several curves (FIG. 1) which are termed as lordosis (convex anteriorly and concave posteriorly) and kyphosis (concave anteriorly and convex posteriorly).

Current surgical treatments for spinal disorders range from removal of regions of the vertebral body (laminectomy) to fusion of adjacent verterbral bodies to replacement of the intervertebral disc with an artificial disc. Newer therapies for treating back pain include ablation of nerves within the vertebral body or thermal coagulation of tissue with the intervertebral disc. Other therapies include using mechanical constructs attached to the spinal processes to stabilize the spine during flexion/extension. Some of the interventions are major surgical procedures with significant morbidity, failure rates and complications; while others address the symptoms (pain) without altering the underlying the cause of the disorder—unstable spine biomechanics.

SUMMARY OF DISCLOSURE

Selectively placed implants are used to address pathologies of the spine arising from improper force distribution. By using appropriately sized and positioned implants as described herein, displacement of targeted connective and muscle tissues surrounding the vertebrae is accomplished in order to realign force vectors and/or alter moment arms loading the spine to achieve therapeutic effects without cutting bone and with minimal cutting of the connective tissues.

In addition to the implants and related prosthesis and apparatus described, embodiments of the present invention include methods of treating spinal disorders and methods of installing implants and prostheses for less invasive spinal treatments. The embodiments of the present invention may be used in conjunction with other spinal therapies like fusion, laminectomy, vertebroblasty, kyphoplasty etc.

One of the exemplary methods disclosed herein comprises selecting at least one of the associated muscle and connective tissues surrounding the vertebrae as target tissue for treatment, and displacing the target tissue without severing the bones or target tissue, thereby redistributing loading within the intervertebral joint to achieve a therapeutic effect. The therapeutic effect could result from changes in the loading of the vertebral bodies or the nucleus pulposus of the intervertebral disc or the annulus of the intervertebral disc.

In another exemplary embodiment of the invention, an apparatus for treating spinal disorder by altering the force distribution in the joint is disclosed. The apparatus is configured and dimensioned for placement in a therapeutic location proximate to a target tissue surrounding the vertebrae and has a thickness sufficient to displace the target tissue from its natural path to a therapeutic path when placed in the therapeutic location. The change in the force distribution may be in the vertebral bodies or the nucleus pulposus of the intervertebral disc or the annulus of the intervertebral disc. Specific structures, configurations, dimensions and fixation modalities are described in more detail herein below.

In a further exemplary embodiment, an apparatus for treating disorders of the spine comprises a prosthesis configured to be mounted to at least one vertebral body in the spine in engagement with a target tissue. The target tissue may comprise at least one posteriorly positioned connective tissue of the spine, wherein the prosthesis is configured and dimensioned so as to displace the connective tissue sufficiently to alter the location, angle or magnitude of forces exerted thereby on a target vertebral body so as to achieve a therapeutic effect in the spine. Displacement of the connective tissue may shift an instantaneous axis of rotation of the target vertebral body dorsally. The shift maybe at least about 3 mm. The prosthesis may be mounted to the target vertebral body or to a vertebral body different from the target vertebral body.

The target connective tissue may include the erector spinae muscle. In certain embodiments, the prosthesis is configured and dimensioned to displace the target tissue from a pre-treatment anatomical path by a displacement distance of more than about 10 mm. In other embodiments the prosthesis may comprise a fixation portion configured to be mounted to at least one vertebral body at a fixation site, a displacement portion configured to engage and displace the target tissue, and a spanning section between the fixation portion and the displacement portion. The spanning section may be configured and dimensioned to position the displacement portion with respect to the target tissue for displacement.

In yet another exemplary embodiment of the present invention, an apparatus for treating disorders of the spine may comprise a prosthesis configured to be located adjacent at least one vertebral body in the spine in engagement with a target tissue targeted for intervention. The target tissue may comprise at least one posteriorly positioned connective tissue of the spine, and the prosthesis may be configured and dimensioned so as to displace that connective tissue sufficiently to alter the location, angle or magnitude of forces exerted thereby on a target vertebral body so as to achieve a therapeutic effect in the spine. Such an exemplary embodiment may also include further features as summarized above and explained in more detail below.

Exemplary embodiments of the present invention may also include methods of treating the spine to reduce loading in a targeted region of the spine. In one such embodiment exemplary steps may comprise selecting at least one of the muscles or connective tissues extending posteriorly along the spine as target tissue for treatment, and implanting a device along the spine so as to displace said target tissue sufficiently to alter the location, angle or magnitude of forces exerted thereby such that loading in said targeted region is reduced.

In further exemplary embodiments of methods according to the present invention, the step of displacing may comprise securing a prosthesis to at least one vertebrae, wherein the prosthesis is configured and dimensioned to displace said target tissue by a distance of more than about 10 mm posteriorly from a pre-treatment anatomical path. Such methods may be directed at target tissues comprising the erector spinae muscles. The step of displacing the target tissue may further involve repositioning an instantaneous axis of rotation of a vertebral body dorsally by at least 3 mm By using appropriately sized and positioned implants and methods as described herein, displacement of targeted connective and muscle tissues surrounding the vertebrae is accomplished in order to realign force vectors and/or alter moment arms loading the joint to achieve therapeutic effects without cutting bone and with minimal cutting of the connective tissues. Alternative and more specific methodologies are described in more detail herein below.

BRIEF DESCRIPTIONS OF DRAWINGS

For the purpose of illustrating the invention, the drawings show aspects of one or more exemplary embodiments of the invention. However, it should be understood that the present invention is not limited to the precise arrangements and instrumentalities shown in the drawings, wherein:

FIG. 1 is a lateral view of the spine.

FIG. 2A is a top view of the intervertebral disc.

FIG. 2B is a perspective view showing a portion of a functional spinal unit (FSU)—two adjacent vertebrae and the intervertebral disc. The adjoining ligaments between them are not shown.

Figure 3A:
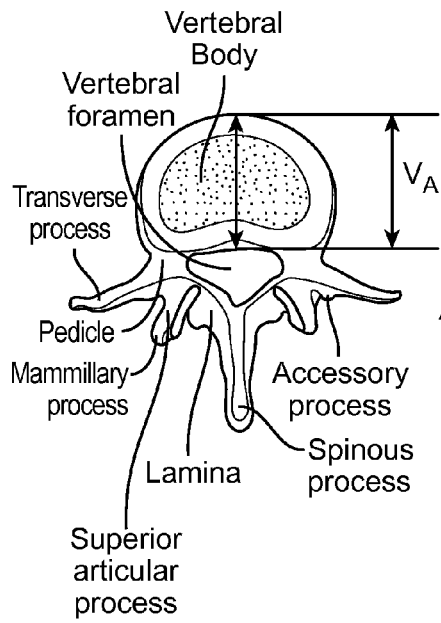
Figure 3B:
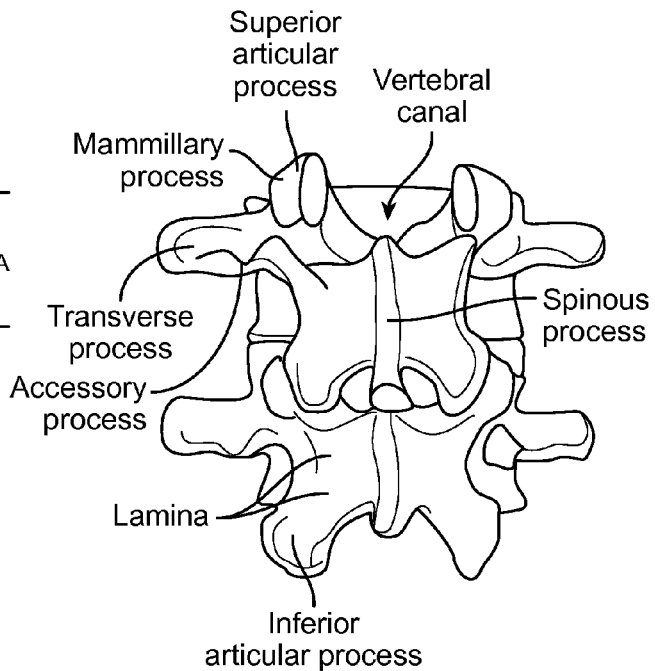

FIGS. 3A-B show the superior view and posterior view of the lumbar vertebrae. $V_A$ represents the depth of the lumbar vertebral body in the anterior/posterior or dorsal/ventral direction.

Figure 4A:
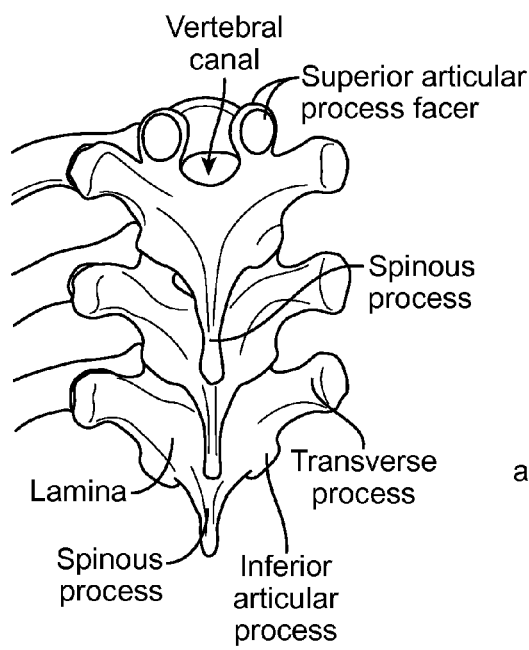
Figure 4B:
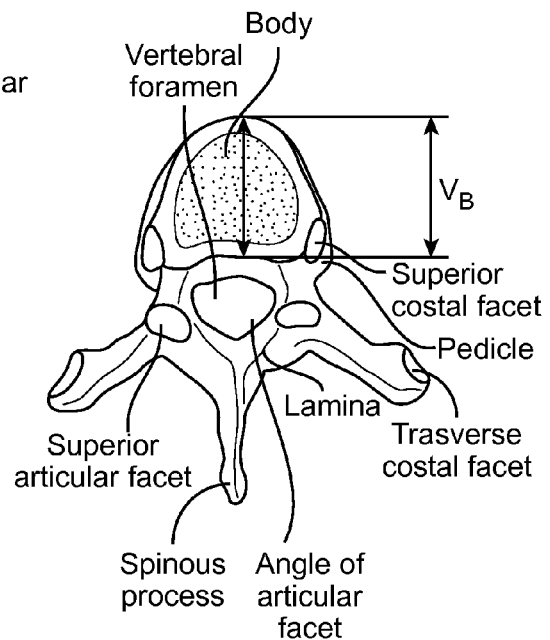

FIGS. 4A-B show the superior view and posterior view of the thoracic vertebrae. $V_B$ represents the depth of the thoracic vertebral body in the anterior/posterior or dorsal/ventral direction.

Figure 5:
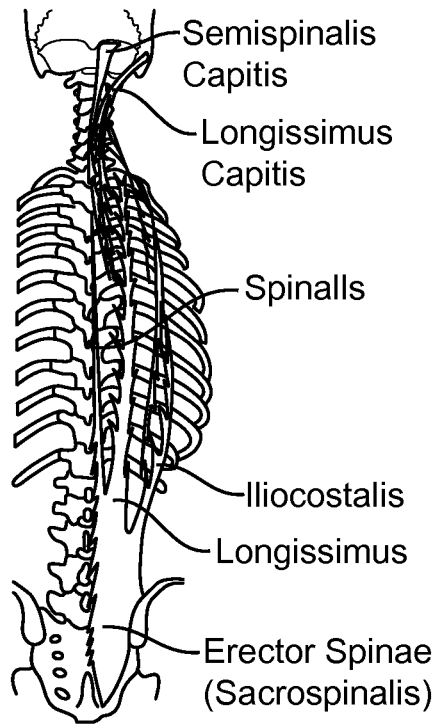

FIG. 5 is a posterior view of the erector spinae muscle.

Figure 6:
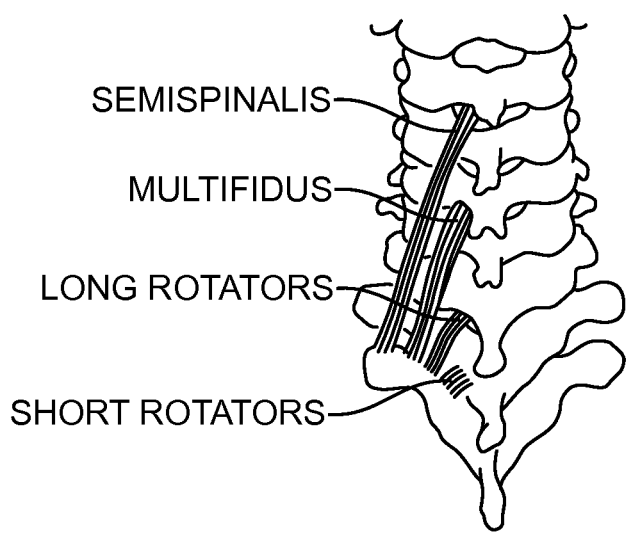

FIG. 6 is a posterior view of the deep layer of the intrinsic back muscles (transversospinal muscles).

Figure 7:
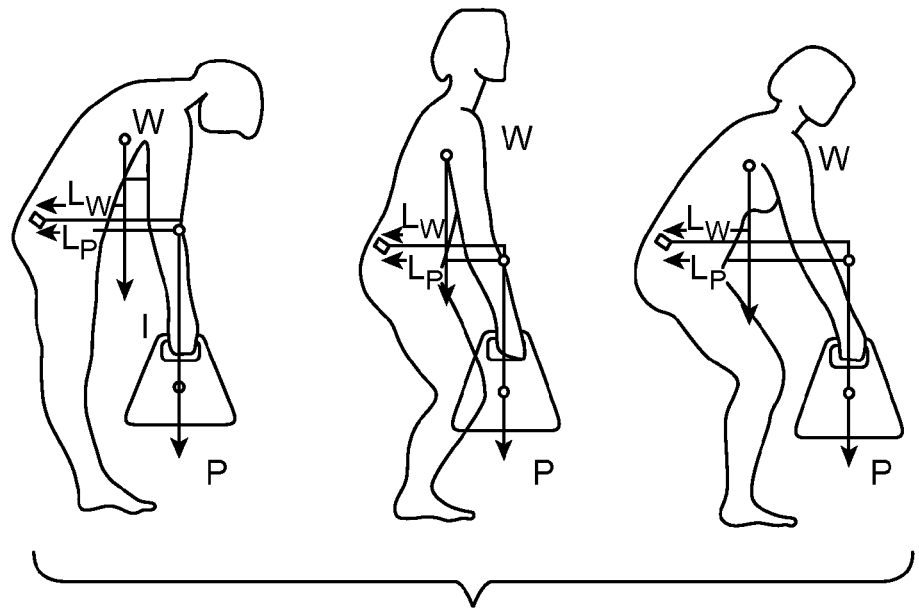

FIG. 7 is a free body diagram illustrating forces acting on a vertebral body during lifting. $L_w$ represents the effective moment arm around a target vertebral body due to the body weight W and $L_p$ represents the effective moment arm around a target vertebral body due to the external weight P.

Figure 8:
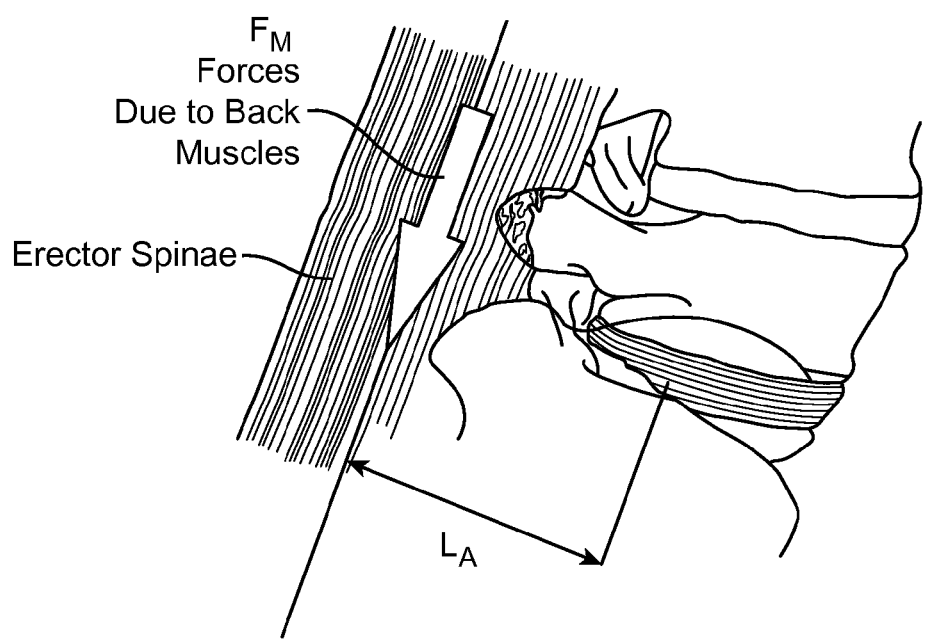

FIG. 8 is a sagittal view of the spine showing the moment arm of the erector spinae muscles for generating a muscle moment to counteract the forward bending moment. $L_A$ represents the effective moment arm.

FIG. 9 is a schematic representation of the instantaneous axis of rotation (IAR) through the vertebral body/intervertebral disc.

FIG. 10 is a sagittal view depicting the concentration of the compressive load in the anterior region of the spinal column due to the forward bending moment.

Figure 11A:
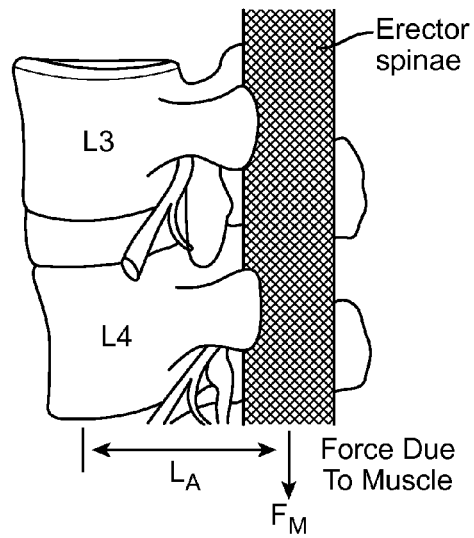
Figure 11B:
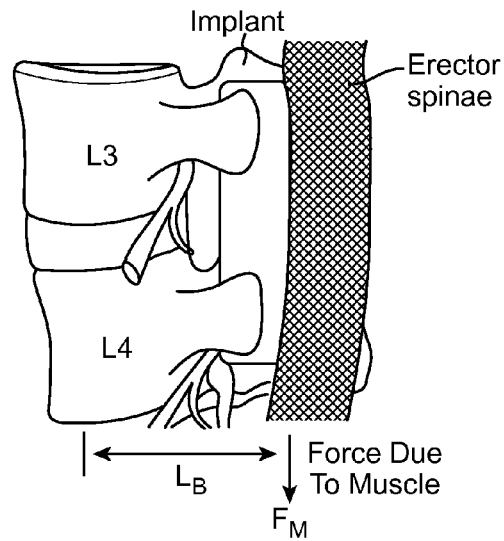

FIGS. 11A-B are sagittal views of the spine depicting the location of the erector spinae muscles before and after placement of an implant according to an exemplary embodiment of the present invention. $L_A$ represents the moment arm of the erector spinae muscles without the implant and $L_B$ represents the resulting moment arm after placement of the implant.

Figure 12:
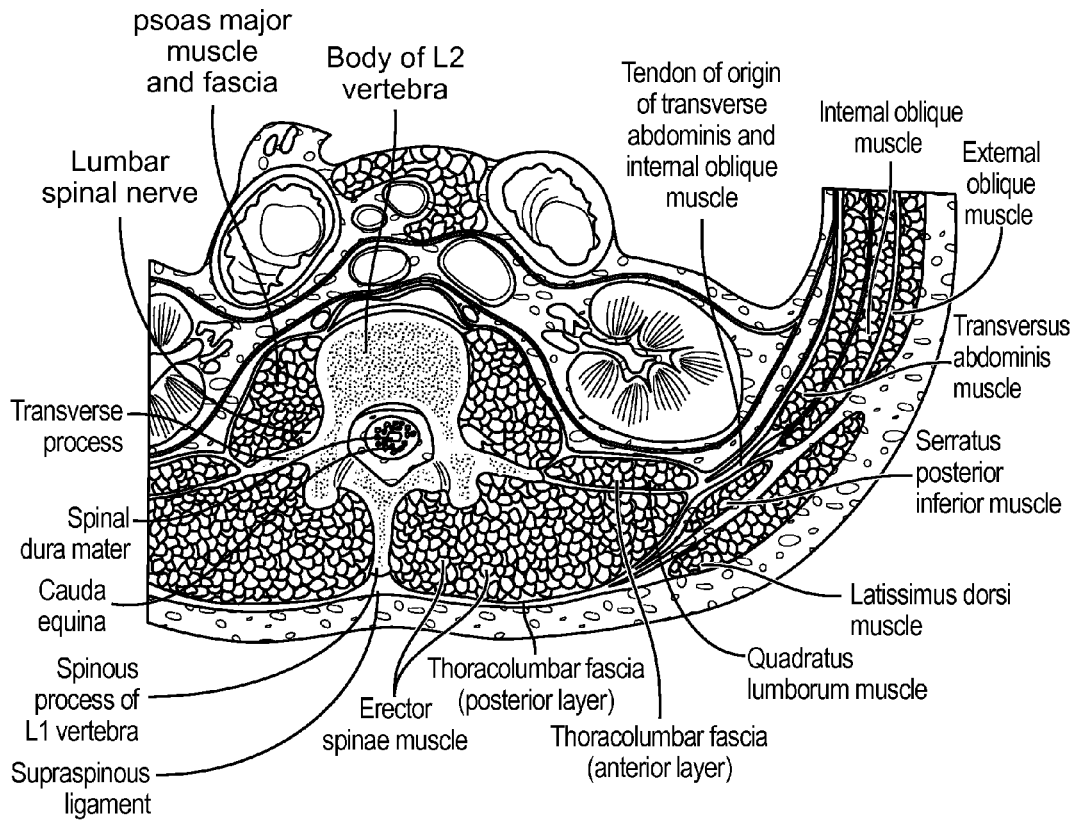

FIG. 12 is a superior view of the cross-section of the lumbar spine illustrating some of the connective tissues and muscles according to embodiments of the present invention.

Figure 13:
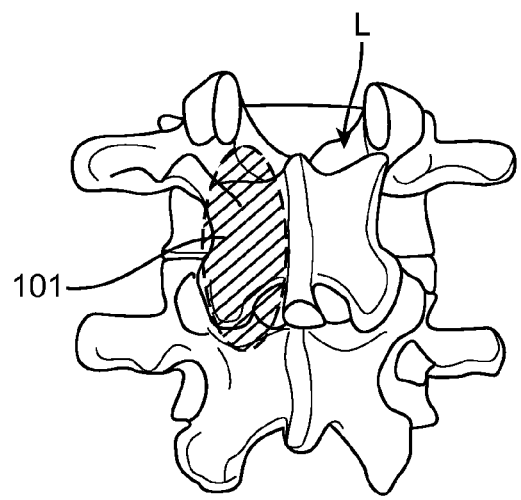

FIG. 13 is the posterior view of the spine with a schematically-illustrated implant according to an exemplary embodiment of the present invention.

Figure 14:
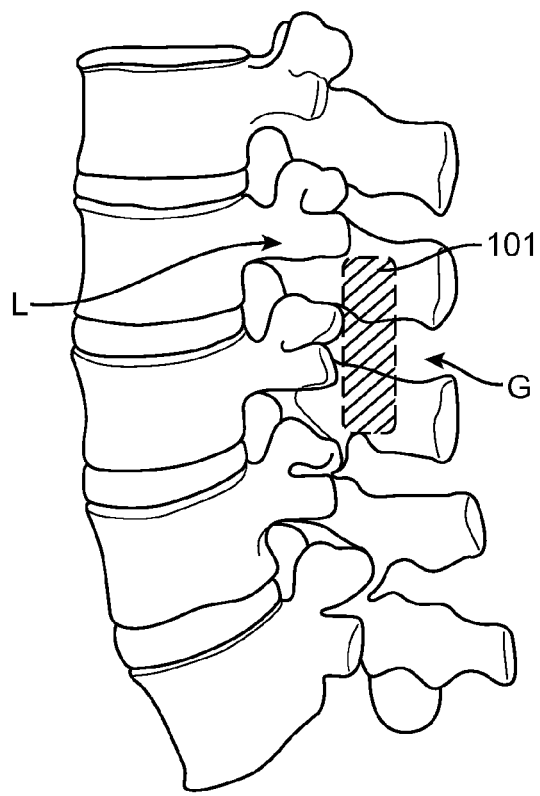

FIG. 14 is the sagittal view of the spine with a schematically-illustrated implant according to an exemplary embodiment of the present invention.

Figure 15:
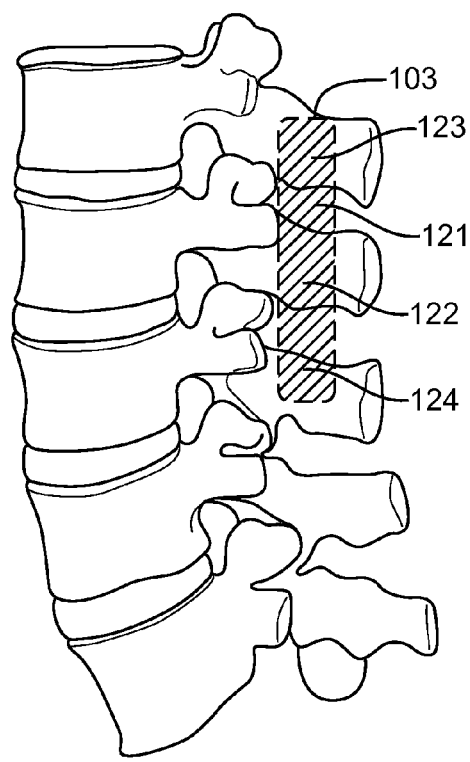

FIG. 15 is the sagittal view of the spine with a schematically-illustrated implant according to an exemplary embodiment of the present invention.

Figure 16:
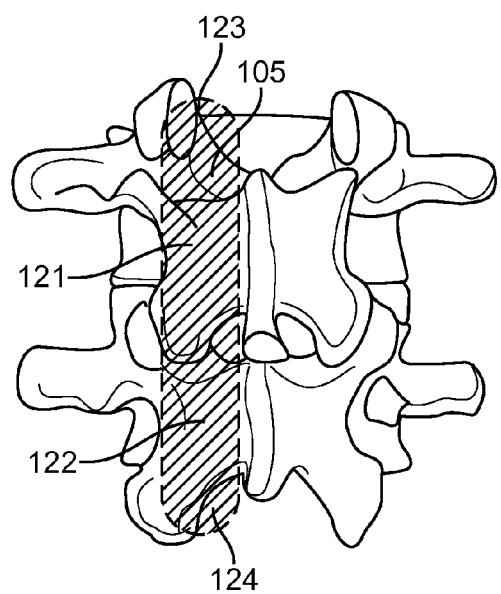

FIG. 16 is the posterior view of the spine with a schematically-illustrated implant according to an exemplary embodiment of the present invention.

Figure 17:
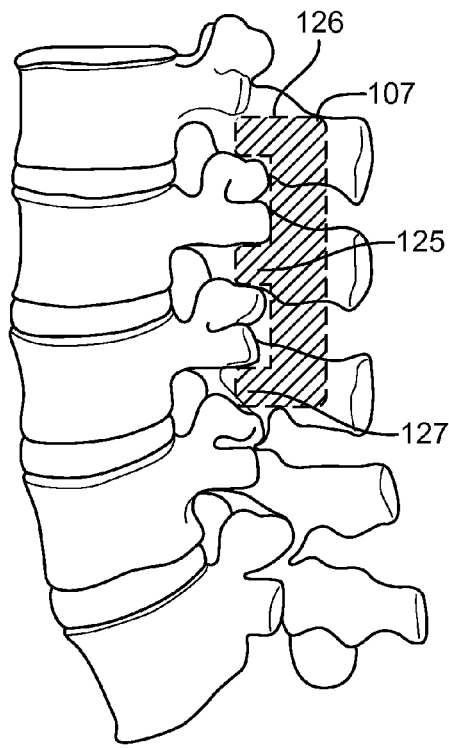

FIG. 17 is the sagittal view of the spine with a schematically-illustrated implant according to an exemplary embodiment of the present invention.

Figure 18:
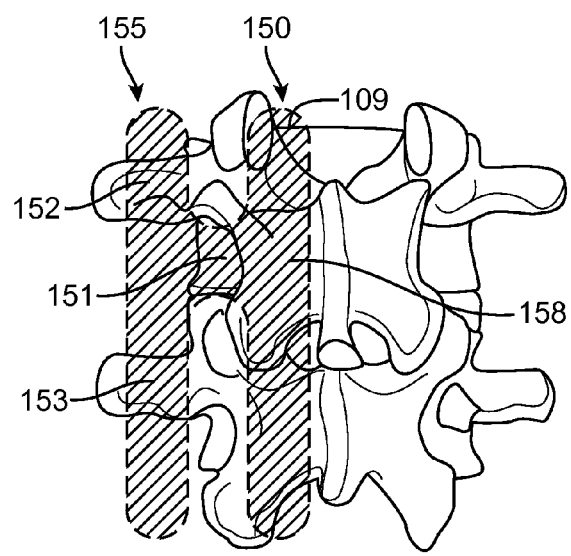

FIG. 18 is the posterior view of the spine with a schematically-illustrated implant according to an exemplary embodiment of the present invention.

Figure 19:
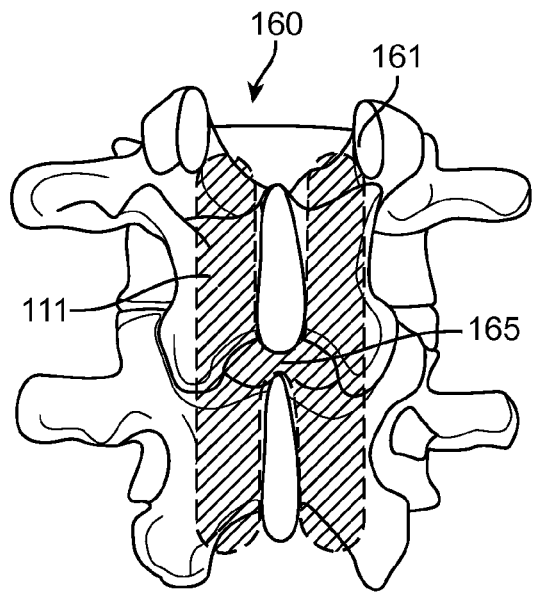

FIG. 19. is the posterior view of the spine with a schematically-illustrated implant according to an exemplary embodiment of the present invention.

FIGS. 20, 21, 24, 25, 28, 28A, 29, 30, 31 and 32 are side views of prostheses according to alternative exemplary embodiments of the present invention.

FIGS. 22, 23, 26 and 27 are plan views of prostheses according to alternative exemplary embodiments of the present invention.

FIGS. 33, 34, 35, 36, 37 and 38 are side views of prostheses according to alternative exemplary embodiments of the present invention, wherein bones A, B and C represent cross-sectional views of adjacent vertebrae.

DETAILED DESCRIPTION

Spinal conditions that result from or exacerbate unbalanced force distribution through the intervertebral joint or the vertebral body may be addressed in embodiments of the present invention by interventional techniques involving a redistribution of forces exerted on the joint without the need for highly invasive surgeries requiring significant trauma to the joint and associated muscle and connective tissues. In some embodiments of the invention, increased forces can be selectively applied to one side of a joint by forcing select muscle and/or connective tissues (target tissues) around a longer or more angled path, thus increasing the magnitude, altering the effective direction, and/or changing the moment arm of forces exerted by such muscles or tissues on the joint. This may be accomplished, for example, by appropriately shaped implants that may be placed under selected target tissues relatively non-invasively compared to current surgical techniques for addressing such conditions. Target tissue may include muscles, tendons or ligaments surrounding the spine.

Before addressing more details of exemplary embodiments of the present invention, it is helpful to have a basic understanding of the anatomy and biomechanics of the spine.

Anatomy of the Spine

The spinal column consists of seven cervical vertebrae (C1-C7) in the neck, twelve thoracic vertebrae (T1-T12) in the upper back, five lumbar vertebrae (L1-L5) in the lower back, five bones (that are "fused" together in adults) to form the bony sacrum and three to five bones fused together to form the coccyx or tailbone (FIG. 1). Each vertebra consists of a large vertebral body in the front, two strong bony areas called pedicles connected to the vertebral body, and bony posterior structures like the spinous process, the transverse process, etc. The main purpose of these structures is to protect the spinal cord, and to enable the connection of the vertebrae to muscles and ligaments. The vertebral body consists of hard exterior shell (cortical bone), with spongy bone (cancellous bone) inside.

The intervertebral discs are fibrocartilaginous cushions serving as the spine's shock absorbing system. Intervertebral discs are composed of an annulus fibrosus and a nucleus pulposus (FIGS. 2A and 2B). The annulus fibrosus is a strong radial tire-like structure connected to the vertebral end plates. The annulus fibrosus encloses the nucleus pulposus. Both the annulus fibrosus and nucleus pulposus are composed of water, collagen, and proteoglycans (PGs). The nucleus pulposus contains a hydrated gel-like matter that resists compression.

The smallest physiological motion unit of the spine is the functional spinal unit (FSU). A FSU consists of two adjacent vertebrae, the intervertebral disc and all adjoining ligaments between them and excludes other connecting tissues such as muscles. The two adjacent vertebrae and intervertebral disc also cooperate to form a joint permitting articulation of the spine.

The spinal column consists of the cervical, thoracic and lumbar segments. Each vertebrae of the lumbar segment (FIGS. 3A and 3B) comprises the vertebral body, the spinous process and the transverse processes. Each vertebral body is attached to a bony arch comprised of two pedicles and two laminae that form a hollow archway (the foramen). The vertebral arches are interconnected by paired, fixed facet joints. The spinous process protrudes from the junction of the two laminae. Transverse processes project from the junction of the pedicles and lamina. $V_A$ represents the depth of the lumbar vertebral body in the anterior/posterior or dorsal/ventral direction. A vertebra of the thoracic segment is shown in FIG. 4a-b. The rib cage is connected to each level of the thoracic spine. $V_B$ represents the depth of the thoracic vertebral body in the anterior/posterior or dorsal/ventral direction. $V_B$ represents the depth of the cervical vertebral body in the anterior/posterior or dorsal/ventral direction (figure not shown). In the human spine, the $V_A$ ranges from about 35 mm to about 55 mm, $V_B$ ranges from about 25 mm to about 40 mm, and $V_C$ ranges from about 10 mm to about 25 mm.

The spine has four major muscles—forward flexors (anterior), lateral flexors (lateral), rotators (lateral) and extensors (posterior). See, for example, FIGS. 5, 6 and 12.

The deep back muscles (intrinsic back muscles) are grouped into superficial, intermediate, and deep layers depending on their proximity to the surface. The superficial layer includes the splenius capitis and cervicis muscles. The intermediate back muscles that act as the primary spinal extensors are the erector spinae muscles. The erector spinae muscles are on either side of the vertebral column within the posterior and anterior layers of the thoracolumbar fascia. The erector spinae muscles straighten a flexed column, and release during its flexion so that the motion is slow and controlled. The erector spinae muscles originate at the sacrum and extend through the lumbar, thoracic and cervical spine. In the lower spine the erector spinae appears as a single muscle. In the upper lumbar area the erector spinae split into three vertical columns (FIG. 5), iliocostalis (lateral), longissimus (intermediate) and spinalis (medial). The iliocostalis is named regionally—the iliocostalis lumborum, thoracis and cervicis. The longissimus is named regionally—the longissimus thoracis, cervicis and capitis. The spinalis is named regionally—the spinalis thoracis, cervicis and capitis. The erector spinae muscles are covered by fascia that attach medially to the spinous processes, and laterally to the transverse processes of the cervical and lumbar vertebrae, and to the ribs. The deep layer of the intrinsic back muscles are also known as the transversospinal muscle group, and include the semispinalis, multifidus, and rotatores muscles (FIG. 6). These shorter muscles are situated deep to the erector spinae and run obliquely. They originate from the transverse processes of a vertebrae and attach to the spinous processes of a more superior vertebrae. The muscles of the semispinalis cross six vertebrae, the multifidus cross four vertebrae, and the rotatores cross one or two vertebrae.

In addition to the muscles described above, there is another group of back muscles that are referred to as the minor deep layer muscles. The interspinalis muscles pass between adjacent spinous processes and the intertransversii muscles pass between adjacent transverse processes.

Biomechanics of the Spine

Loads on the spine are primarily a result of body weight, muscle activity and externally applied loads. In general, the line of gravity of the trunk runs ventral to the axis of the spine, hence, the spine is subjected to a constant forward bending moment. This forward bending moment is counteracted by ligament forces and the posterior erector spinae muscles. During daily activities like lifting, the bending moment on the spine is influenced by the external loads as well as the body posture during lifting (FIG. 7). As shown in FIG. 8, the forward bending moment which includes body weight and any external load, is counteracted by the posterior extensor muscle moment (force times the moment arm of the muscle force). The moment arm of the posterior extensor muscle is the distance between the effective line of action of the erector muscle and the instantaneous axis of rotation (IAR) through the vertebral body/intervertebral disc (FIG. 9). When the forward bending moment is large or the erector spinae muscles are weak, IAR moves ventrally (anteriorly), leading to excessive compressive forces in the anterior region of the vertebral column (FIG. 10). Excessive loading of the anterior spine leads to degeneration of the intervertebral disc which is the cause of disc degenerative disease (DDD). In addition, excessive bending moment may increase the chance of failure, particularly in osteoporotic bone, at the site of maximum bending moment and force application (FIG. 9). After the initiation of failure ventrally such failure usually propagates dorsally. These compression fractures are a significant source of pain to the patient.

Exemplary methods disclosed in this invention comprises selecting at least one of the associated muscle and connective tissues surrounding the vertebrae as target tissue for treatment, and displacing the target tissue without severing the bones or target tissue, thereby redistributing loading within the intervertebral joint to achieve a therapeutic effect. In some embodiments, the target tissues are displaced posteriorly.

One of the benefits of the methods and devices in the present invention is that, compared to current treatments, the significantly lower surgical morbidity could be beneficial to patients showing early as well as advanced symptoms of spinal disorders. Additionally, the methods and devices of the present invention could be beneficial for patients with weak or osteoporotic bone. As used herein, "therapeutic effect" means an effect on a treated FSU that reduces or redistributes forces acting on the FSU or target bone structures, in particular the joint formed by the cooperation of the vertebrae and discs, decreases pain or provides another positive outcome for the patient whether across an FSU or in particular parts of an FSU. "Therapeutic effect," however, does not imply, and should not be understood as requiring, any specific, quantified outcome other than as stated above. "Therapeutic location" as used herein refers to a location where a prosthesis or implant is placed in accordance with embodiments of the present invention to achieve a therapeutic effect. Similarly, "therapeutic path" refers to a path of target tissues over the implant or prostheses according to embodiments of the present invention that is displaced from the normal anatomical path of the tissue so as to achieve a therapeutic effect.

As used herein, in humans, dorsal refers to the back of an organism and ventral to the belly. Cranial refers to the head end and caudal to the tail end. In humans, anterior is used to indicate the ventral surface and posterior is used to indicate the dorsal surface. Superior means toward the head and inferior means toward the feet. Proximal refers to the end of a structure nearest a major point of reference and distal refers to the end of a structure furthest from a point of reference. The point of reference is usually the origin of a structure (such as a limb). Proximal and distal are relative terms. Medial means nearer the midline of the body and lateral means further from the midline of the body. Superficial refers to structures nearer the skin, and deep to structures further away from the skin. A sagittal plane divides the body into right and left (or medial and lateral) parts. A frontal (or coronal) plane passes from right to left and divides the body into dorsal and ventral (or posterior and anterior) parts. A transverse plane (or cross section) passes perpendicular to the long axis of the body and divides the body into cranial and caudal (head and tail) portions.

Exemplary embodiments of the invention described herein are particularly directed to treatment of the human spine. In general, it will be appreciated by persons of ordinary skill in the art that specific features described in connection with one exemplary embodiment may be incorporated in other exemplary embodiments unless otherwise noted. The exemplary embodiments described are thus included to illustrate features of the invention, not limit it.

FIGS. 11A and 11B illustrate an exemplary embodiment of the present invention with a schematically-illustrated implant according to one embodiment positioned along the posterior of the vertebral body to assist in redistributing the forces acting on vertebral body/intervertebral disc to provide a therapeutic effect. As shown therein, an implant placed adjacent to the vertebral body forces the target tissues that run there along to assume a more posterior path. That longer path may have a number of beneficial effects, including increasing the moment arm of the target tissue. As a result, the effective posterior moment is increased to more effectively counter the forward bending moment. This moves the IAR dorsally (or posteriorly), away from the anterior of the vertebral body/intervertebral disc. The amount of displacement of the target tissue need not be large in order to potentially have a substantial effect on moving the instantaneous axis of rotation. Dependent upon the geometry of a particular patient's spine, posterior displacements of between about 10 mm to about 50 mm may be preferred, more preferably in the range of about 15 mm to about 45 mm, most preferably in the range of about 20 mm to about 40 mm.

In some embodiments, the implants of the present invention move the IAR measured during flexion by more than 3 mm dorsally, more preferably by more than 6 mm dorsally, most preferably by more than 9 mm dorsally. As will be evident to one skilled in the art, the relationship between the dorsal displacement of the IAR and the therapeutic effect will depend on the multiple factors including the size of the vertebral body (e.g.; $V_A$, $V_B$ and $V_C$), the location of the vertebral body (cervical, thoracic or lumbar), the state of the adjacent intervertebral discs, the state of the adjacent intervertebral bodies, the location of the IAR prior to treatment etc.

The location of the prosthesis may be at the same spinal level as the one being treated or could be located at a spinal level more cranial or caudal to the one being treated. The prosthesis may also span multiple spinal vertebrae.

It is proposed that by placing an implant under the deep back muscles to displace the muscles posteriorly, the moment arm of the force vectors can be increased to counter the anterior forces. In certain embodiments, an implant is placed on either side of the spinal process. The implant acts as a spacer to displace the tissue posterior to the spine. In some embodiments, the erector spinae muscles are displaced posteriorly. By increasing the moment arm of the erector spinae muscles, the force acting through the vertebral body/intervertebral disc could be redistributed to reduce the excessive loading on the anterior vertebral body (FIG. 10). By increasing the moment arm of the erector spinae muscles, the IAR would move dorsally, leading to reduced compressive forces in the anterior region of the vertebral column. The redistribution of the force could alleviate pain associated with degenerative disc disease and could slow down or halt the degeneration of the disc. In osteoporotic vertebrae, by redistributing the forces and reducing the compressive load on the anterior region of the vertebral body, the risk of compression fracture of the vertebral body may be decreased.

In some embodiments, the implant may be attached to the vertebral body, the articular process, the transverse process, the spinous process, the lamina, the facet, the pedicle or any other bony structure of the vertebrae using screws, hooks, bands, sutures, wires, etc. The implants may be attached to the vertebral body at a single location or at multiple locations. The implants may be attached only in the cranial region or only in the caudal region. The implant may be attached to bone located medial to the implant or lateral to the implant. In other embodiments, the implant may be attached to bone ventral to the implant or dorsal to the implant. Implants may be attached to a vertebral body located away from the vertebral body/segment being treated. Implants may have sections or features for tissue displacement (displacement portion or segment), sections or features for fixation (fixation portion or segment), and a spanning portion that connects the displacement portion and the fixation portion. The displacement segment, the spanning segment and the fixation segment may be in alignment with each other or may be displaced from each other. The displacements or offset between the segments may be cranial, caudal, lateral, medial, ventral, dorsal, oblique etc. Implants may be rigid or substantially rigid or soft compliant prostheses secured to adjacent bone or the surrounding tissues.

In general, such implants may be rigid, semi-rigid or soft compliant prostheses secured to adjacent bone or the surrounding tissues. Rigid or substantially rigid prostheses according to embodiments of the invention described herein could be made of known bone-compatible implant materials such as titanium or stainless steel. Biocompatible polymers, ceramics, and other materials may also be used. The bearing surface of the prostheses should be designed to minimize negative effects of movement of the connective tissues across the implant surface, having a low coefficient of friction with no or minimal rough edges, corners, or discontinuities. Such prostheses could be implanted arthroscopically or using a mini-open or open surgical approach.

Implants also may be held in place by the surrounding tissues without using a fixation element. Soft compliant prostheses could be filled with water, saline, silicone, hydrogels, etc., sufficient to move the tissue laterally (relative to the direction of force exerted by such tissue) as described above. Such a soft compliant prosthesis could be placed in a deflated state and then inflated to the appropriate thickness. Alternatively, implants may be filled with other flowable materials including beads or other particles made of metal, polymer, or foam material, optionally in a liquid medium, which conform to the adjacent bone or tissue surfaces. The implant could be inflated with a curable material, such as a polymer, which is substantially liquid for a period of time during the implantation procedure, but then cures into a harder permanent state. Thixotropic materials, such as hydrogels derived from hyaluronic acid, change their mechanical properties as shear stress is applied to them. An implant filled with such materials could be made to change the amount of displacement that it provides based on the shear stress that it sees from overlying target tissues during flexion/extension. Implants may be coated with materials to reduce friction such as hydrophilic coatings or polytetrafluoroethylene (PTFE) coatings. Additionally or alternatively, the prosthesis may be adjustable to allow the dimensions such as thickness of the prosthesis to be adjusted during surgery or any time after surgery. Rigid or substantially rigid prostheses could be made of known bone-compatible implant materials such as titanium or stainless steel. Biocompatible polymers, ceramics, and other materials may also be used. Coatings like titanium nitride, titanium niobium nitride etc. may be used to increase wear resistance, lubricity etc. Whether rigid or compliant, the surface of the prosthesis should be designed to minimize negative effects of movement of the connective tissues across the implant surface. Such prosthesis could be implanted arthroscopically or using a mini-open or open surgical approach.

In various alternative embodiments, the displacement portion and the fixation portion of prostheses according to the invention may be of unibody construction, or may be formed of two or more parts depending on desired function. For example, the fixation portion may be stainless steel or titanium textured to enhance bony ingrowth and solid screw fixation, while the bearing/displacement portion could be made of a different material, for example, pyrolytic carbon to enhance the ability of overlying tissues to slide across the implant, or PTFE, silicone or other low-friction polymer with suitable wear characteristics to provide a softer bearing surface. In further alternatives, the displacement portion could be comprised of a substrate of one material with an overlying layer forming the bearing material. The substrate could be either attached to or contiguous with the fixation portion. In other embodiments, the fixation portion of the implant may have a relief feature to minimize contact with the underlying bone, thereby minimizing disruption of the periosteal layer.

The bearing surface may be hard and smooth, made from materials such as polished pyrolytic carbon, steel, or titanium, or coated or covered with a lubricious material, such as PTFE. It might alternatively be designed to encourage adhesion and ingrowth of the connective tissue onto this surface. For example the surface may be porous, roughened, or configured with openings into which bone or scar tissue may grow to enhance adhesion.

The implant could have a shape or feature adapted to guide the muscles and tendons and retain their position on the implant. For example, a groove or trough could be provided on the outer surface of the prosthesis through which the muscles and tendons would extend. These muscles and/or tendons are aligned with the groove when the implant is installed. Alternatively, the implant could include a ring or eyelet with a discontinuity to allow placement of the ring or eyelet around the muscles/tendons. Implants may have also varying thickness so as to provide varying displacement of the muscles and tendons.

In some embodiments, the implant could be anchored to the underlying bone with suitable fasteners such as screws. Depending on the location and surgical need, unicortical screws, bicortical screws, cancellous screws, cannulated screws, polyaxial screws, screws that lock into the implant etc. may be used. In some embodiments, the screw holes may be locking threads or other locking features. In other embodiments, the screw holes may be oriented in different directions to improve the stability of the anchored implant. In alternate embodiments, different types of screws may be used in different regions of the implant.

In some embodiments, implants may also be placed without securing it to surrounding tissues, for example without placement of bone-penetrating screws. In some embodiments, the device may be held in place solely by its position between the vertebral body and the vertebral muscles. For example, the device may be contoured to fit in between certain spinal processes, with certain features to prevent it from sliding superiorly or inferiorly. It could also be held in that location by the muscles on top of it.

Soft compliant prostheses could be filled with water, saline, silicone, hydrogels etc. sufficient to displace tissue as described above. Such a soft compliant prosthesis could be placed in a deflated state and then inflated to the appropriate thickness. Additionally or alternatively, the thickness of the prosthesis may be adjusted during surgery or at any time after surgery. Rigid or substantially rigid prostheses could be made of known bone compatible implant materials such as titanium or stainless steel.

Implants on either side of the spinous process may be identical or different. Implants on either side of the spinous process may be independent (without any connecting segment) or could be connected with a connecting section. The connecting segment may be rigid, substantially rigid or flexible. Such asymmetric implants may be useful in treating scoliosis or spines with mild lateral bending.

In some embodiments, extension, rotation, and lateral bending are not affected. In other embodiments, extension, rotation and lateral bending may be minimally affected.

The methods and devices of the present invention may be used to treat a variety of spinal disorders. For example, for treatment of spinal sagittal plane instability resulting from degenerative spondylolisthesis or surgical decompression or laminectomy. In some embodiments, the treatment could be directed towards instability due to ligament laxity. Alternatively, the methods and devices may be used to alleviate pain related to forward bending in patients with degenerative disc disease (DDD). In some embodiments, pain associated with extension, rotation and lateral bending may be alleviated.

The methods and devices of the present invention may result in reduced segmental motion during flexion and increased spinal stability during flexion. Alternatively, the methods and devices may increase flexion stiffness. In some embodiments, the methods and devices may increase facet engagement.

In some embodiments, the devices and methods of the present invention do not bear or transmit axial compressive loads on the spine.

The methods and devices of the present invention could be compatible with decompression for patients suffering from lumbar spinal stenosis, for example, laminotomy, facetectomy or foraminotomy. The devices could also be used in conjunction with spinous process sparing surgeries and in surgeries where the part or all of the spinous process is removed.

The implants of the present invention may be considered to be permanent implants that remain in the patient for many years or implants that are used temporarily for short duration of a few months for temporary pain reduction or to enable recovery from an adjunct spinal surgery. For example, the devices of the present invention may be used as a permanent or temporary implant in conjunction with vertebroplasty or kyphoplasty to stabilize the spinal segment that underwent vertebroplasty or kyphoplasty. Alternatively, the devices may be used to stabilize adjacent spinal segments to minimize the incidence of adjacent segment disease (e.g.; vertebral fracture, disc degeneration etc.) after vertebroplasty or kyphoplasty.

In some embodiments, the devices may be used to address sagittal or translation instability in spinal segments adjacent to segments that have undergone fusion surgery or segments that are stiff.

Implants of the present invention may take many forms as discussed in more detail below with respect to various exemplary embodiments of the present invention.

FIGS. 13-19 schematically depict the general size, shape, and location on the spine of implants according to exemplary embodiments of the present invention. In some embodiments (e.g., FIG. 13-17), while the implant is shown on one side of the spinal processes, implants also may be placed on either or both sides of the spinous process. Implant 101, schematically shown in FIGS. 13-14, is located posterior to the vertebral body in a region generally as shown, which may be in contact with the lamina (L), displacing the posterior muscles. Implants in embodiments of the present invention may span about the height of a vertebral body, the height of the lamina (L), or the gap (G) between two transverse processes, or may extend cranially and/or caudally beyond the adjacent transverse processes as in implants 103 and 105 shown in FIGS. 15 and 16. The lateral width of the implant may cover about the width of the lateral gutter or part of the lateral gutter. The implant may be placed medially in contact with the spinous processes or more laterally in contact with the articular processes or in contact with both the processes or with no contact to either process. Different regions of the implant may have different surface features, cross-sectional shapes, surface textures etc. Additionally, different regions of the implant may have different heights or thicknesses. For example, as shown for implants 103 and 105, region 121 and 122 which are in contact with the underlying lamina may have thickness greater than regions 123 and 124. Alternatively, regions 123 and 124 may be thicker. In some embodiments, for example implant 107 in FIG. 17, the implant may have extensions (127, 126 and 125) that reside in the notches between the vertebral bodies thereby providing resistance to implant displacement during flexion/extension.

FIG. 18 depicts a schematically-illustrated embodiment of the invention, wherein implant 109 extends laterally outside the articular process and displaces tissue posterior to the transverse processes. Two displacement segments 150 and 155 may be connected with a connecting segment 151. Segment 151 may be flexible or rigid. The height of the connecting segment 151 may be such that it is in contact with the articular process of the superior and inferior vertebrae or alternatively, it may be narrow such that it does not contact the articular processes and does not interfere with any spinal motion. Displacement segment 155 may also have regions with different surface features, cross-sectional shapes, surface textures, thicknesses etc. For example, regions 152 and 153 in contact with the transverse process may be thicker compared to the rest of displacement segment 155.

Figure 26:
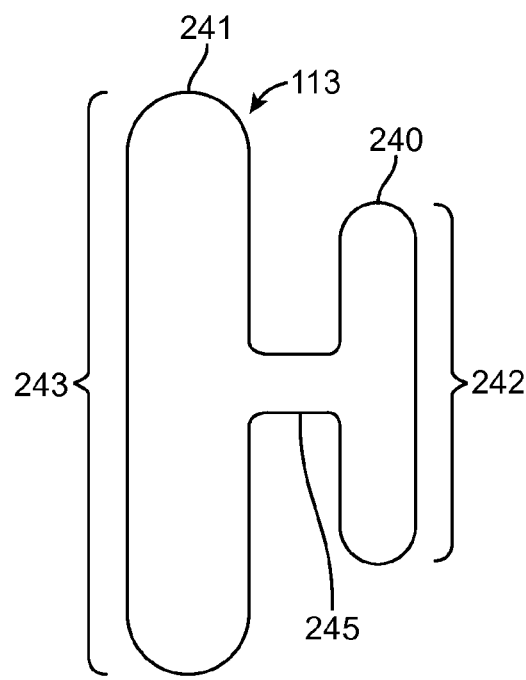
Figure 27:
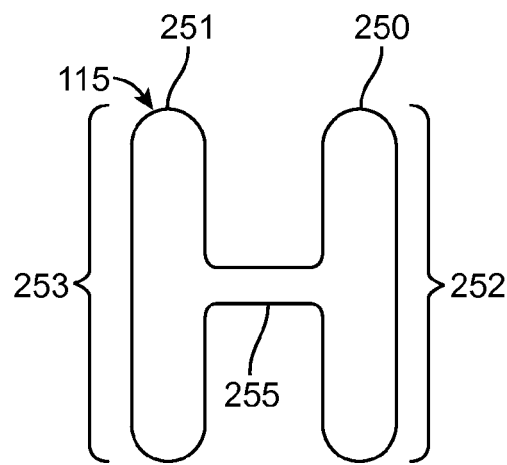

FIG. 19 schematically depicts a further embodiment in which implant 111 extends bilaterally on either side of the spinous process. Two displacement segments 160 and 161 are connected with a connecting segment 165. Segment 165 may be flexible or rigid. The height of the connecting segment 165 may be such that it is in contact with the spinous process of the superior and inferior vertebrae or alternatively, it may be narrow such that it does not contact the spinous processes and does interfere with any spinal motion. Further alternative embodiments are shown in FIGS. 26 and 27. In FIG. 26, implant 113 has displacement sections 241 and 240 with different dimensions 243 and 242 joined by connecting segment 245 as shown to accommodate various anatomic variations as may be encountered in different patients. Similarly, implant 115 shown in FIG. 27 includes displacement sections 250 and 251 of the same dimensions 252 and 253 joined by connecting segment 255.

In some embodiments, devices of the present invention may be placed under the multifidus muscles, in contact with the posterior surface of the vertebral body structures. In other embodiments, devices of the present invention may be placed above the multifidus muscles, in contact with the erector spinae muscles.

Figure 20:
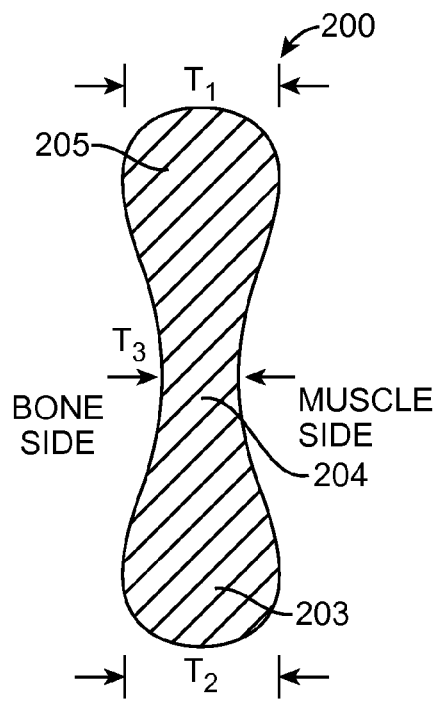
Figure 21:
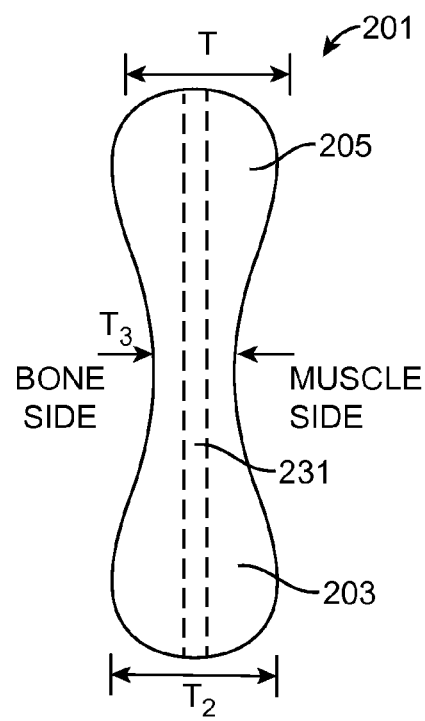

FIG. 20 (implant 200) and 21 (implant 201) show further exemplary embodiments of devices of the present invention. The thickness of the implant may vary along the length of the implant, in the cranial/caudal direction. For example, regions 205 and 203 ($T_1$ and $T_2$) may be thicker or wider than region 204 ($T_3$) thereby displacing the target soft tissue more in certain locations around the target vertebral body than in other locations. In other embodiments (FIG. 24), the end regions 211 and 213 ($T_x$ and $T_z$) may be thinner or narrower than middle region 212 ($T_y$) of implant 220.

In other exemplary embodiments, implant 201 (FIG. 21) or implant 230 (FIG. 25) may have a lumen 231 to enable guiding the implant percutaneously to the target location. In inflatable embodiments, the implant may be inserted and guided in a deflated state. Once the implant position is confirmed (for example, with radiographic markers on the implant), the implant may be inflated to achieve the appropriate tissue displacement. The implant may be filled with a liquid or gas under suitable pressure to allow displacement of the target tissue. The implant may have one or more hollow chambers defined by an outer wall (e.g. at 232 in FIG. 25), and an inflation port for introduction of inflation fluid by means of an inflation device, which may be a syringe, pump, or a device similar to the inflation devices used for inflation of angioplasty balloons as will be understood by persons of ordinary skill in the art.

Figures 28, 28A:
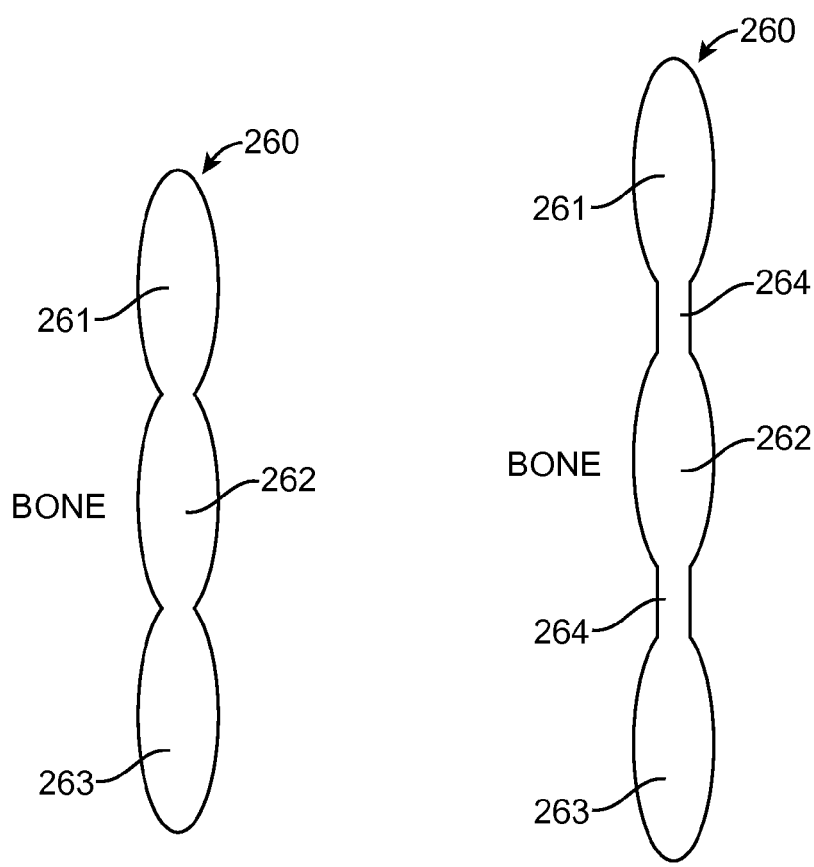
Figure 29:
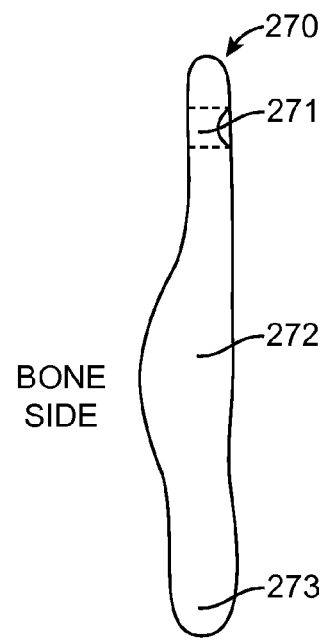

In another embodiment, an implant 260 may have separate chambers 261, 262 and 263 (FIG. 28). These separate chambers will allow the placement of a single implant to distract soft tissue from multiple vertebrae, while still permitting appropriate bending motion of the spine. In a further alternative, illustrated in FIG. 28A, flexible, extensible, compressible tubular sections 264 are provided between each chamber 261, 262, 263. The tubular sections between the chambers may facilitate positioning by allowing each chamber to remain in a fixed position relative to its associated vertebrae during flexion, extension, and sideways bending of the spine. Implant 260 may be temporarily inflated with air, saline, or other medium allowing appropriate visualization with the imaging modality being used. Once appropriate positioning and displacement of tissue is confirmed, the temporary inflation medium can be removed and replaced with a permanent inflation material such as a curable polymer or hardening cement, two-part epoxy, or other suitable material. The tubular sections 264 may be provided with inflation lumens communicating with each chamber from a proximal end, and a lumen to hold a semi-rigid pusher or stiffening wire to help advance the implant into position.

In some embodiments, the implant may be anchored to a single vertebral body. The implant may be attached using screws, anchors, hooks, wires etc. The implant may have one or more features for coupling to an anchoring device, such as a loop, hole, or channel. For example, implant 270 (FIG. 29) may be anchored using a screw placed through a hole 271 near either the superior or inferior end of the implant. Enlarged portion 272 may be configured and dimensioned to be received in a depression between adjacent vertebrae or otherwise specially configured to match a corresponding space in in the patient anatomy. Inferior end 273 may be unattached after implantation.

Figure 30:
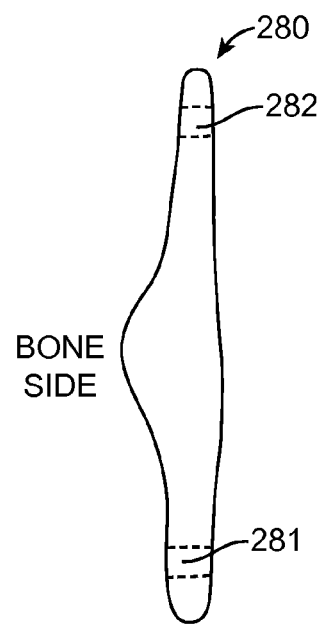
Figure 31:
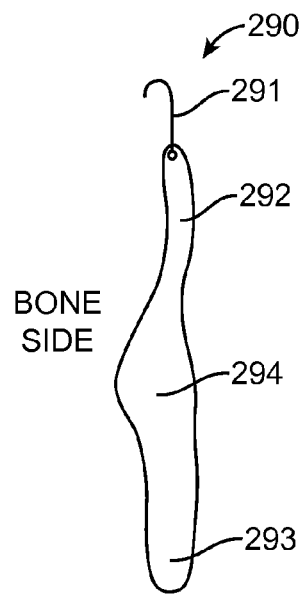

In other embodiments multiple screws may be used to anchor the implant to a single vertebral body, such as through holes 281, 282 near opposing ends of implant 280 (FIG. 30). The screws could be placed in through the pedicle, the lamina or any other bony region of the vertebrae. In some embodiments, the implant may be anchored using a hook, for example implant 290 (FIG. 31) may be anchored using one hook 291 near its superior end 292. The hook may be configured to anchor to the articular process, the transverse process, the spinous process, the lamina, the pedicle or any other bony structure of the vertebrae. In the example illustrated, inferior end 293 is not provided with an attachment means. In other embodiments multiple hooks may be used to anchor the implant to a single vertebral body. In other embodiments, a combination of anchoring elements may be utilized on the same vertebral body. Once again, enlarged portions 283 or 294 may be configured and dimensioned to match a corresponding profile in the patient anatomy.

Figure 32:
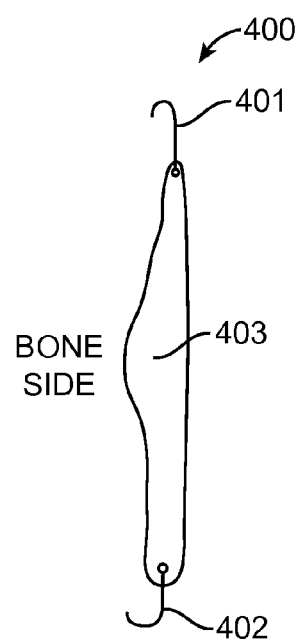

In some embodiments, multiple anchoring elements may be used to anchor the implant to multiple vertebrae (FIG. 32). Hooks 401, 402 may be coupled to the implant 400 at the opposing superior and inferior ends, respectively. An enlarged portions 403 also may be provided in this embodiment.

The implants described herein in accordance with various embodiments of the invention may be used with cervical, thoracic or lumbar vertebrae. Implants may be placed at one level or at multiple levels of the spine. Implants may span a single level or multiple levels of the spine.

Other exemplary embodiments of the present invention, comprising implants 300, 310, 420, 410, 405, 430, 440, and 450 are shown, respectively, in FIGS. 22, 23, 33-38. In some embodiments, the implants may be substantially rigid. The implants may have three regions, a fixation region for attaching the implant to surrounding tissue, a displacement region that displaces the target tissue and a spanning section that interconnects the fixation and displacement regions.

Implant fixation portions 312 (FIG. 23), 301 (FIG. 22), 421 (FIG. 33), 411 (FIG. 34), 408 (FIG. 35), 431 (FIG. 36), 441 (FIG. 37) and 451 (FIG. 38) may be configured to be anchored to the underlying bone using screws (S) placed through bone screw holes 303, 311, 422, 412, 409, 432, 442, and 452, respectively. Depending on the mechanical load on the implant, and the choice of material or materials used to fabricate the implant, thickness of fixation portion of the implant may vary. The thickness of the fixation portion of the implant may be uniform or may vary. Regions of the fixation portion under higher mechanical load may be thicker than regions under lower mechanical loads. The thickness of the fixation region may also be selected to ensure that the screw-heads used to fix the implant do not protrude over the surface of the implant so as to protect adjacent tissues from injury.

Spanning sections 314 (FIG. 23), 423 (FIG. 33), 413 (FIG. 34), 407 (FIG. 35), 433/435 (FIG. 36), 443 (FIG. 37) and 453 (FIG. 38) may have thickness similar to that of the fixation portion. Bone A, Bone B and Bone C in the figures schematically represent cross-sectional views of adjacent vertebrae. Persons of ordinary skill in the art will appreciate that a principal consideration for the spanning section is sufficient structural integrity to maintain the displacement portion of the desired treatment position. In the displacement portion, displacement distance and thickness may be considered separately. Displacement distance is the distance by which the bearing surface of the displacement portion extends beyond the natural anatomical track of the target tissue, in other words, the magnitude of displacement of tissue created by the implant. Depending on the particular geometry of the implant, the thickness of the displacement portion may or may not be related to the displacement distance. For example, in some embodiments (see, e.g. FIGS. 33, 34, 35, 36, 37 and 38), the thickness of the displacement portion (424, 414, 406, 434/436, 444/445 and 454, respectively) may be substantially less than the overall displacement distance D. In these embodiments, the displacement portion may be elevated off the underlying bony surface of the vertebrae and may be preferred to minimize any disruption of the periosteal layer.

Figure 37:
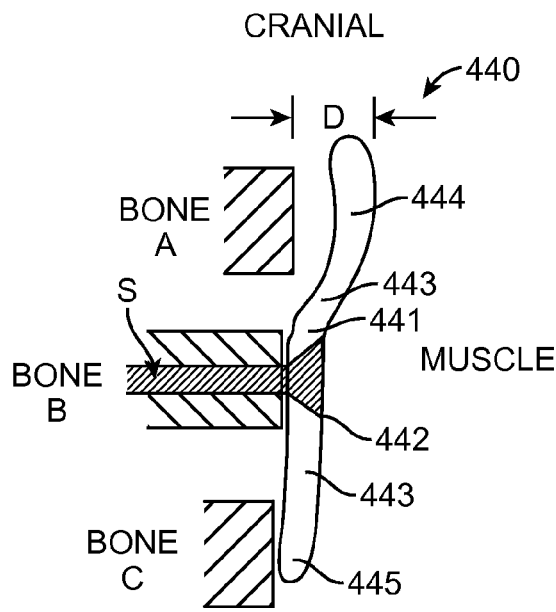

In other embodiments, the thickness of the displacement portion and the tissue displacement may be identical, whereby the displacement portion of the implant is in contact with the underlying bone, as, for example, shown in FIG. 37 with displacement portion 445.

In some embodiments, displacement distance across the displacement portion may vary. As further examples of how displacement distance and thickness may relate, the displacement portion may be in contact with the underlying tissue and the target soft tissue is displaced by a distance equivalent to the thickness of the displacement portion; thus displacement distance would equal thickness in such an embodiment. In other embodiments, the displacement portion may be elevated above the underlying tissue and the target soft tissue is displaced by a distance greater than the thickness of the displacement region; thus displacement distance is greater than thickness.

In some embodiments, the implant may have two or more spanning sections 433 and 435 (FIG. 36) connecting a fixation section 431 to a plurality of displacement portions 434, 436. The tissue displacements $D_1$ and $D_2$ of the displacement portions may be the same or different. In another example, implant 440 (FIG. 37) includes one displacement portion 444 spaced from the underlying bone and second displacement portion 445 on the underlying bone.

In some embodiments of the present invention, the displacement of the connective tissue could be adjusted by adjusting the device pre-operatively, intra-operatively or post-operatively. The spanning sections may also comprise adjustable mechanisms (e.g. a pin, jack, screw, inflatable member, hydraulic piston, or hinge) to movably or pivotably alter the orientation or angle between the fixation section and the displacement section (for example, 453 in FIG. 38) to achieve the appropriate level of tissue displacement, In various adjustable embodiments described above, the adjustment mechanisms themselves may be radiopaque and/or otherwise discernible from the rest of the implant under x-ray in order to enable post-surgical percutaneous adjustment of the device. Alternatively, target features can be built into the device to locate the adjustment points without having the screws or adjustment means themselves radiopaque, such as radiopaque rings or markers built into the bearing surface of the device itself.

Devices may include electric, pneumatic, or hydraulic motors or actuators to alter the displacement that may be remotely controlled, including by mechanisms that enable wireless communication to alter the displacement after implantation. Alternatively, the displacement may be adjusted by applying an energy field (e.g.; magnetic field, electric field, thermal field etc.) transdermally from an external location.

Figure 23:
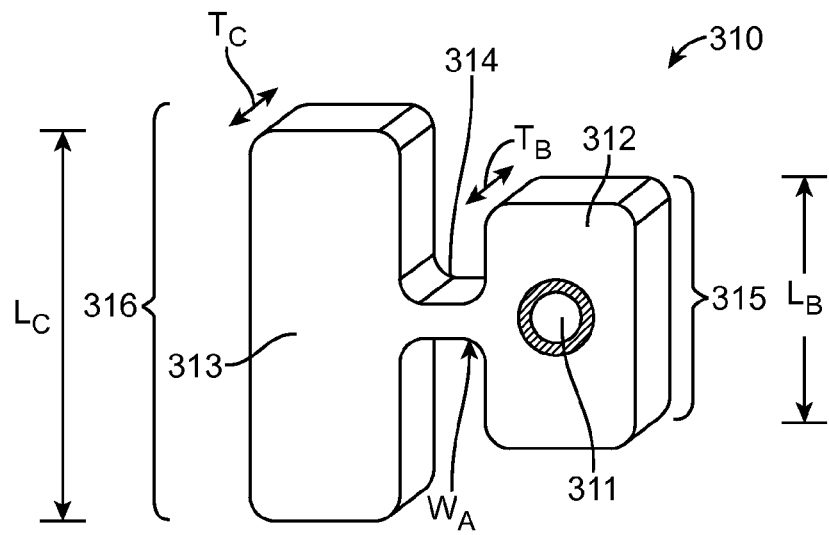
Figure 24:
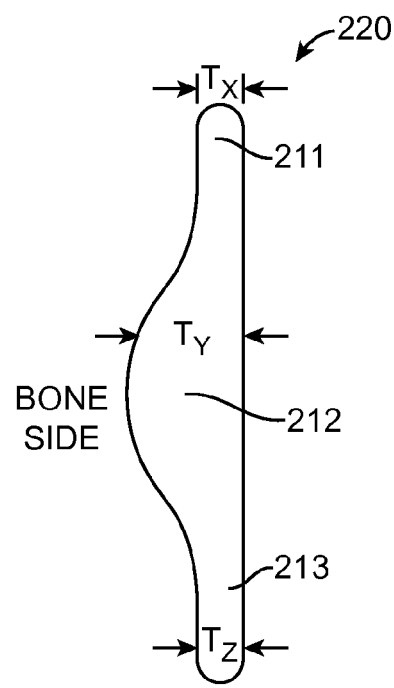
Figure 25:
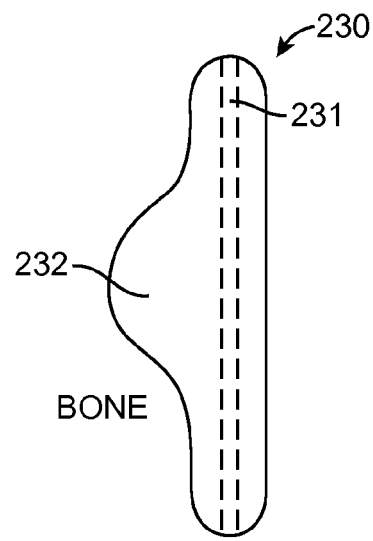
Figure 33:
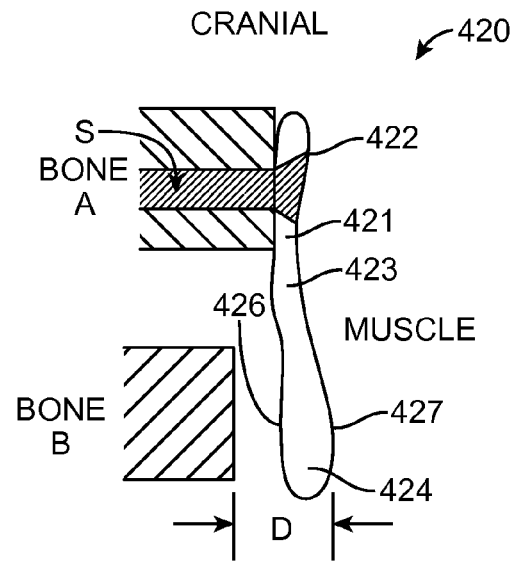
Figure 34:
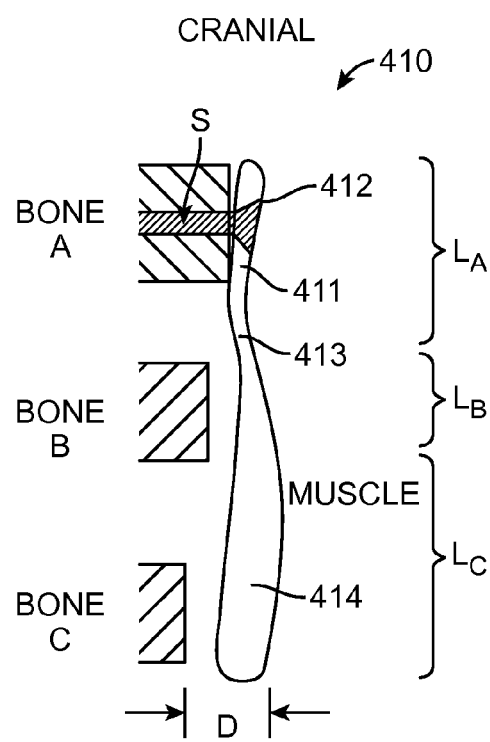
Figure 35:
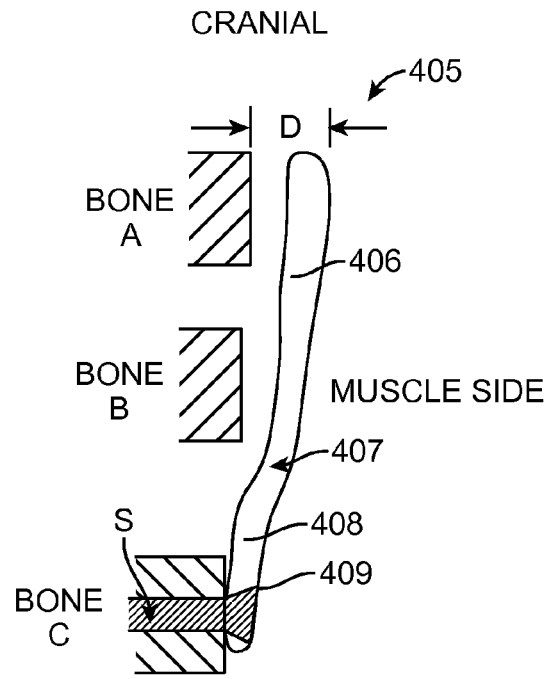
Figure 36:
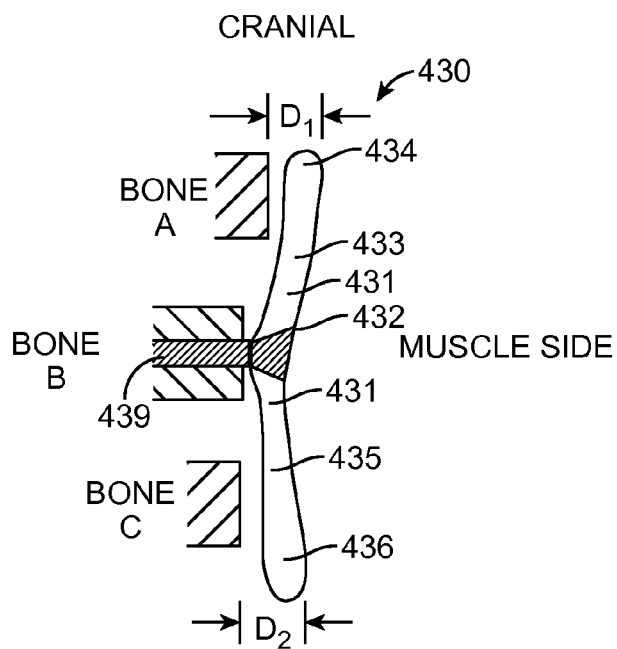
Figure 38:
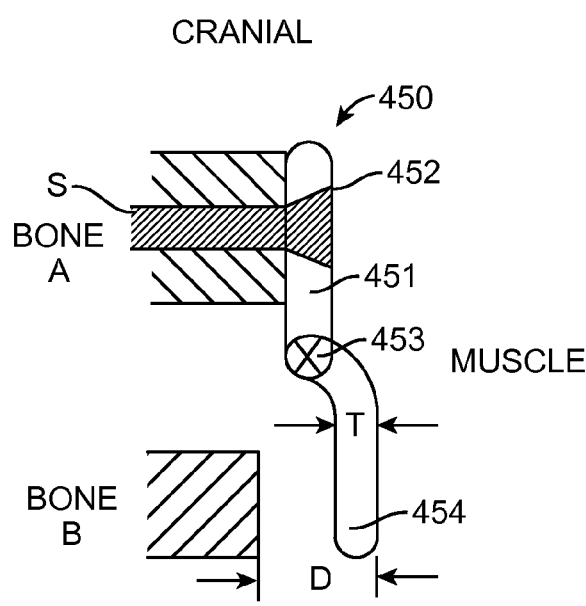

In some embodiments, the fixation portion may be cranial to the displacement portion (e.g.; FIGS. 33, 34 and 38). In other embodiments, the fixation portion may be caudal to the displacement portion (e.g.; FIG. 35). In other embodiments, there may be displacement section cranial and caudal to the fixation portion (e.g.; FIGS. 36 and 37). In other embodiments, the fixation portion may extend cranially or caudally from the location of the anchoring element 1 (e.g.; FIG. 37). In yet other embodiments the displacement section may be offset laterally relative to the fixation portion (FIG. 23).

In some embodiments, implants of the present invention may be anchored to the target vertebral body. In some embodiments, the target intervertebral disc may be cranial to the vertebral body to which the implant is anchored. In other embodiments, the target intervertebral disc may be caudal to the vertebral body to which the implant is anchored. In some embodiments, the implants of the present invention may be anchored cranial or caudal to the target vertebral body. In some embodiments, the target vertebral body may be one spinal level caudal or one spinal level cranial to the vertebral body used to anchor or fix the implant. In some embodiments, the target vertebral body may be two or more spinal levels caudal or two or more spinal levels cranial to the vertebral body used to anchor or fix the implant.

Figure 22:
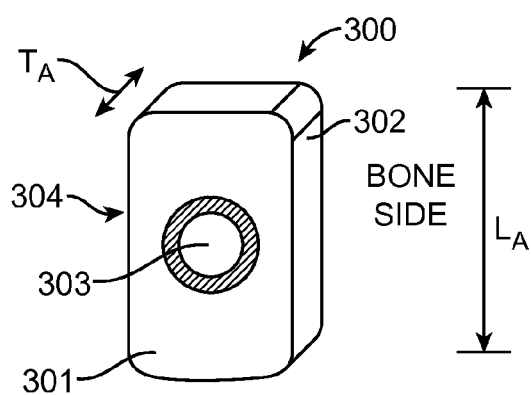

In some embodiments, the fixation portion, the spanning portion and/or the displacement portion, or portions thereof, may be aligned, i.e. stacked on top of each other or overlapping in the ventral-dorsal direction (e.g. implant 300 in FIG. 22).

In some embodiments, the implant may be anchored to a single vertebral body. The implant may be attached using screws, anchors, wires etc. For example, implant 300 (FIG. 22) and implant 310 (FIG. 23) may be anchored using screws placed through a hole 303 and 311 in the implants, respectively. A bone-facing implant surface 302 could be concave to make good contact with the underlying bone of the vertebral body. Alternatively, the bone-facing surface may include spikes, ridges, bumps, barbs, or other textural features to enhance the anchoring of the implant. The bone-facing surface may also be coated with an ingrowth promoting agent or may inherently have a porous structure to enable bone ingrowth. The posterior surface of the implant 304, which is in contact with soft tissue (multifidus muscles, erector spinae muscles etc.) may be smooth, low-friction, and free of sharp edges or protrusions to avoid tissue injury, and may be contoured to be concave or otherwise shaped to ease the motion of the muscle during flexion/extension of the spine. The radius of curvature of the concave surfaces on the anterior and posterior sides of the implant may be identical or different. The radius of curvature of each surface may also vary along the length of the implant, in the cranial/caudal direction. The thickness of implant 300, $T_A$ in FIG. 22, could be constant or variable in the cranial/caudal and medial/lateral directions. In another embodiment, the thickness of displacement portion 313 and fixation portion 312 ($T_B$ and $T_C$ in FIG. 23) could be identical or different. The thickness of the connecting segment 314 could constant or variable to bridge the difference in thicknesses of the two segments. The lateral distance between sections 312 and 31 ($W_A$) also may be varied. In some embodiments, the connecting segment 314 may also be a spanning section, connecting the displacement portion 313 with the fixation portion 312. In some embodiments, the displacement portion 313 may also have a secondary fixation region, including a screw hole or other means for anchoring the displacement region 313 to bone. The lengths of each segment 315 ($L_B$) and 316 ($L_C$) could be identical or different. In some embodiments, $L_B$ could be greater than $L_C$. In other embodiments, $L_C$ could be greater than $L_B$. In some embodiments, $L_B$ and $L_C$ may span the height of one vertebral body. In other embodiments, $L_B$ and $L_C$ may span more than one vertebral body.

In some embodiments, the anterior surface of the implant may also be contoured in the medial/lateral direction to conform to the contours of the posterior surface of the vertebral body.

In some embodiments, the implant may have features to enable it to be attached to the surrounding soft tissue, thereby preventing any dislocation of the implant. For example, the prosthesis may have an attached suture that can be wrapped around the target soft tissue.

The surface of the implant could be modified as needed for interaction with the soft/hard tissue. For example, the surface could be smooth to allow for easy movement of the soft tissue across the surface. Alternatively, the surface may have an adhesive surface to allow attachment to underlying bone or soft tissue. The surface could be coated with a hydrophilic or hydrophobic layer. The surface may have a polymeric coating for drug release. Drugs like anti-inflammatory drugs and antibiotics could be incorporated into the polymeric coating.

In those embodiments where the implant spans several vertebrae, it may have design features which accommodate the relative motion of the vertebrae. For example, since the posterior aspects of the vertebrae become closer and more distant as the spine is flexed and straightened, it may be advantageous to have an implant with vertebral sections which hold their position relative to each vertebra, either by fixation, adhesion, shape, or other means, such as having features which interact with the spinous processes on each vertebrae. This implant could further have intervertebral sections which flex, extend, and compress freely with the motion of the spine. This will prevent longitudinal motion of the implant surface relative to the vertebral bodies. These vertebral and intervertebral sections might not be dramatically different or segregated. For example, the implant might be cast from a relatively flexible, compressible material, with harder elements in the center of this flexible material corresponding to the locations of the vertebrae.

An implant which spans several vertebral bodies may be inserted from one end of the desired implanted location. It would be desirable for vertebral sections of the implant to naturally tend to lock into position relative to each vertebrae and hold that position, so that additional incisions to insert fixation elements are not necessary.

While the invention has been illustrated by examples in various contexts of treating spinal disease associated with force imbalances in the vertebral body/intervertebral in the lumbar spine, it will be understood that the invention may also have application to treatment of spinal disease in the thoracic and cervical spine.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

The invention claimed is:

1. A method of treating the spine to reduce loading in a targeted region of the spine, comprising:
    implanting a prosthesis without cutting bone along a posterior portion of the spine in engagement with an erector spinae muscle adjacent the targeted region, and displacing the engaged erector spinae with said prostheses by at least about 10 mm from a pre-treatment, anatomical path, said displacement being sufficient to alter the location, angle or magnitude of forces exerted the displaced muscle such that loading in said targeted region is reduced.

2. The method of claim 1, wherein said implanting does not limit mobility of adjacent vertebrae relative to the vertebral body during spinal flexion and extension.

3. The method of claim 2, wherein said implanting is accomplished without removing an intervertebral disk.

4. The method of claim 3, wherein said implanting further includes not cutting an interspinalis muscle.

5. The method of claim 1, further comprising dorsally repositioning an instantaneous axis of rotation of a vertebral body dorsally in the target region by at least 3 mm by said displacing.

* * * * *